US010981899B2

(12) United States Patent
Buck et al.

(10) Patent No.: US 10,981,899 B2
(45) Date of Patent: Apr. 20, 2021

(54) INHIBITORS OF SOLUBLE ADENYLYL CYCLASE

(71) Applicants: CORNELL UNIVERSITY, Ithaca, NY (US); Tri-Institutional Therapeutics Discovery Institute, New York, NY (US)

(72) Inventors: Jochen Buck, Old Greenwich, CT (US); Lonny Levin, New York, NY (US); Lavoisier Ramos-Espiritu, Forest Hills, NY (US); Clemens Steegborn, Bayreuth (DE); Ayumu Sato, Zushi (JP); Rei Okamoto, Yokohama (JP); Mayako Michino, New York, NY (US)

(73) Assignees: Cornell University, Ithaca, NY (US); Tri-Institutional Therapeutics Discovery Institute, New York, NY (US)

( * ) Notice: Subject to any disclaimer, the term of this patent is extended or adjusted under 35 U.S.C. 154(b) by 0 days.

(21) Appl. No.: 16/097,087

(22) PCT Filed: Apr. 28, 2017

(86) PCT No.: PCT/US2017/030188
§ 371 (c)(1),
(2) Date: Oct. 26, 2018

(87) PCT Pub. No.: WO2017/190050
PCT Pub. Date: Nov. 2, 2017

(65) Prior Publication Data
US 2020/0157084 A1 May 21, 2020

Related U.S. Application Data

(60) Provisional application No. 62/328,806, filed on Apr. 28, 2016.

(51) Int. Cl.
*C07D 409/14* (2006.01)
*C07D 409/12* (2006.01)

(52) U.S. Cl.
CPC ......... *C07D 409/14* (2013.01); *C07D 409/12* (2013.01)

(58) Field of Classification Search
CPC .. C07D 239/48; C07D 239/28; C07D 409/14; C07D 409/12; A61K 31/506
See application file for complete search history.

(56) References Cited

U.S. PATENT DOCUMENTS

| 3,892,554 A | 7/1975 | Schneider et al. |
| 4,025,515 A | 5/1977 | Schneider |
| 5,280,009 A | 1/1994 | Hamprecht et al. |
| 6,080,750 A | 6/2000 | Hisaki et al. |

| 2004/0229909 A1 | 11/2004 | Kiyama et al. |
| 2007/0244174 A1 | 10/2007 | Buck et al. |
| 2008/0004268 A1 | 1/2008 | Nguyen et al. |
| 2008/0119535 A1 | 5/2008 | Galley et al. |
| 2008/0255172 A1 | 10/2008 | Su et al. |
| 2008/0261990 A1 | 10/2008 | Dittrich-Wengenroth et al. |
| 2010/0035863 A1 | 2/2010 | Raphy et al. |
| 2011/0275611 A1 | 11/2011 | Axten et al. |
| 2011/0305640 A1 | 12/2011 | Buck et al. |
| 2012/0053179 A1 | 3/2012 | Nagarathnam et al. |
| 2012/0202806 A1 | 8/2012 | Durrenberger et al. |
| 2016/0002175 A1 | 1/2016 | Scobie et al. |

FOREIGN PATENT DOCUMENTS

WO 2000063182 A2 10/2000

OTHER PUBLICATIONS

PubChem CID: 47279808 (Nov. 26, 2010).*
PubChem CID 71853735 (Nov. 29, 2013).*
PubChem CID: 71850530 (Nov. 29, 2013).*
PubChem CID: 60500169 (Oct. 18, 2012).*
Hisaki et al., Synthesis and anti-influenza virus activity of novel pyrimidine derivatives, Antiviral Research, Feb. 6 1999, vol. 42, No. 2, pp. 121-137.
Kast et al., Cardiovascular effects of a novel potent and highly selective azaindole-based inhibitor of Rho-kinase, British Journal of Pharmacology, Oct. 15, 2007, vol. 152, No. 7, pp. 1070-1080.
Ramos-Espiritu et al., Discovery of LRE1 as a specific and allosteric inhibitor of soluble adenylyl cyclase, Nature Chemical Biology, Aug. 22, 2016, vol. 12, No. 10, pp. 838-844.
PubChem SID: 299388852, PubChem Open Chemistry Database, Jan. 28, 2016, https://pubchem.ncbi.nlm.nih.gov/substance/299388852.
PubChem SID: 301851888, PubChem Open Chemistry Database, Jan. 28, 2016, https://pubchem.ncbi.nlm.nih.gov/substance/301851888.
6-Chloro-N4-[(furan-2-yl)methyl]-N4-[(thiophen-2-yl)methyl]pyrimidine-2,4-diamine, PubChem Open Chemistry Database, Oct. 18, 2012, https://pubchem.ncbi.nlm.nih.gov/compound/60500169.
PubChem SID: 278548888, PubChem Open Chemistry Database, Jan. 12, 2016, https://pubchem.ncbi.nlm.nih.gov/substance/27854888.
PubChem SID: 166426443, PubChem Open Chemistry Database, Dec. 1, 2013, https://pubchem.ncbi.nlm.nih.gov/substance/166426443.
PubChem SID: 145051303, PubChem Open Chemistry Database, Oct. 18, 2012, https://pubchem.ncbi.nlm.nih.gov/substance/145051303.
PubChem SID: 188995980, PubChem Open Chemistry Database, Jul. 12, 2014, https://pubchem.ncbi.nlm.nih.gov/substance/188995980.
PubChem SID: 262864538, PubChem Open Chemistry Database, Dec. 11, 2015, https://pubchem.ncbi.nlm.nih.gov/substance/262864538.

(Continued)

*Primary Examiner* — Deepak R Rao
(74) *Attorney, Agent, or Firm* — Hodgson Russ LLP

(57) ABSTRACT

Provided are 6-amino substituted 2,6-diamino-4-chloropyrimidine compounds which are specific inhibitors of soluble adenylyl cyclase. The compounds can be formulated with pharmaceutical carriers and used for reducing cyclic AMP levels. The compositions can be used for treatment of various conditions including ocular hypotony.

11 Claims, 19 Drawing Sheets

(56) References Cited

OTHER PUBLICATIONS

6-Chloro-N4-[(furan-2-yl)methyl]-N4-[(5-methylthiophen-2-yl)methyl]pyrimidine-2,4-diamine, PubChem Open Chemistry Database, Nov. 29, 2013, https://pubchem.ncbi.nlm.nih.gov/compound/71884751.
6-Chloro-N4-[(oxolan-2-yl)methyl]-N4-[(thiophen-2-yl)methyl]pyrimidine-2,4-diamine, PubChem Open Chemistry Database, Nov. 29, 2013, https://pubchem.ncbi.nlm.nih.gov/compound/71850530.
PubChem SID: 189585899, PubChem Open Chemistry Database, Jul. 12, 2014, https://pubchem.ncbi.nlm.nih.gov/substance/189585899.
PubChem SID: 165578805, PubChem Open Chemistry Database, Nov. 29, 2013, https://pubchem.ncbi.nlm.nih.gov/substance/165578805.
PubChem SID: 266357231, PubChem Open Chemistry Database, Dec. 11, 2015, https://pubchem.ncbi.nlm.nih.gov/substance/266357231.
PubChem SID: 266357232, PubChem Open Chemistry Database, Dec. 11, 2015, https://pubchem.ncbi.nlm.nih.gov/substance/266357232.
PubChem SID: 188954996, PubChem Open Chemistry Database, Jul. 12, 2014, https://pubchem.ncbi.nlm.nih.gov/substance/188954996.
PubChem SID: 165711971, PubChem Open Chemistry Database, Nov. 29, 2013, https://pubchem.ncbi.nlm.nih.gov/substance/165711971.
6-Chloro-4-N-[2-(diethylamino)ethyl]-4-N-(thiophen-2-ylmethyl)pyrimidine-2,4-diamine, PubChem Open Chemistry Database, Nov. 29, 2013, https://pubchem.ncbi.nlm.nih.gov/compound/71853735.
PubChem SID: 266354384, PubChem Open Chemistry Database, Dec. 11, 2015, https://pubchem.ncbi.nlm.nih.gov/substance/266354384.
PubChem SID: 189584528, PubChem Open Chemistry Database, Jul. 12, 2014, https://pubchem.ncbi.nlm.nih.gov/substance/189584528.
PubChem SID: 165582079, PubChem Open Chemistry Database, Nov. 29, 2013, https://pubchem.ncbi.nlm.nih.gov/substance/165582079.
PubChem SID: 122401591, PubChem Open Chemistry Database, May 20, 2011, https://pubchem.ncbi.nlm.nih.gov/substance/122401591.
PubChem SID: 299398050, PubChem Open Chemistry Database, Jan. 28, 2016, https://pubchem.ncbi.nlm.nih.gov/substance/299398050.
PubChem SID: 130447089, PubChem Open Chemistry Database, Dec. 6, 2011, https://pubchem.ncbi.nlm.nih.gov/substance/130447089.
PubChem SID: 166855249, PubChem Open Chemistry Database, Dec. 1, 2013, https://pubchem.ncbi.nlm.nih.gov/substance/166855249.
PubChem SID: 166989231, PubChem Open Chemistry Database, Dec. 1, 2013, https://pubchem.ncbi.nlm.nih.gov/substance/166989231.
PubChem SID: 130336175, PubChem Open Chemistry Database, Dec. 6, 2011, https://pubchem.ncbi.nlm.nih.gov/substance/130336175.
PubChem SID: 123460917, PubChem Open Chemistry Database, Jun. 21, 2011, https://pubchem.ncbi.nlm.nih.gov/substance/123460917.
PubChem SID: 122002349, PubChem Open Chemistry Database, May 20, 2011, https://pubchem.ncbi.nlm.nih.gov/substance/122002349.
PubChem SID: 116076723, PubChem Open Chemistry Database, Mar. 29, 2011, https://pubchem.ncbi.nlm.nih.gov/substance/116076723.
PubChem SID: 132001164, PubChem Open Chemistry Database, Jan. 24, 2012, https://pubchem.ncbi.nlm.nih.gov/substance/132001164.
PubChem SID: 130339878, PubChem Open Chemistry Database, Dec. 6, 2011, https://pubchem.ncbi.nlm.nih.gov/substance/130339878.
PubChem SID: 123460436, PubChem Open Chemistry Database, Jun. 21, 2011, https://pubchem.ncbi.nlm.nih.gov/substance/123460436.
6-Chloro-N~4~-(thiophen-2-ylmethyl)pyrimidine-2,4-diamine, PubChem Open Chemistry Database, Feb. 9, 2007, https://pubchem.ncbi.nlm.nih.gov/compound/14257468.
PubChem SID: 169515389, PubChem Open Chemistry Database, Dec. 2, 2013, https://pubchem.ncbi.nlm.nih.gov/substance/169515389.
PubChem SID: 309529335, PubChem Open Chemistry Database, Jan. 30, 2016, https://pubchem.ncbi.nlm.nih.gov/substance/309529335.
6-Chloro-N4-[(4-ethylphenyl)(thiophen-2-yl)methyl]pyrimidine-2,4-diamine, PubChem Open Chemistry Database, Nov. 29, 2013, https://pubchem.ncbi.nlm.nih.gov/compound/71940097.
6-Chloro-N~4~-Cyclopropyl-N~4~-4[(Thiophen-2-YI)methyl]pyrimidine-2,4-Diamine, PubChem Open Chemistry Database, https://pubchem.ncbi.nlm.nih.gov/compound/47279808, (2010).

\* cited by examiner e f

INHIBITORS OF SOLUBLE ADENYLYL CYCLASE

CROSS REFERENCE TO RELATED APPLICATIONS

This application claims priority to U.S. Provisional Application No. 62/328,806, filed on Apr. 28, 2016, the disclosure of which is hereby incorporated by reference.

STATEMENT REGARDING FEDERALLY SPONSORED RESEARCH

This invention was made with government support under grant no. R21 EY025810 awarded by the National Institutes of Health. The government has certain rights in the invention.

FIELD OF THE DISCLOSURE

The disclosure generally relates reducing cyclic AMP levels. In particular, this disclosure provides compositions for reducing cAMP action by preferential inhibition of soluble adelylyl cyclase.

BACKGROUND OF THE DISCLOSURE

Cyclic AMP is the prototypical second messenger. It has been implicated in a wide variety of (often contradictory) physiological processes, including cell proliferation, apoptosis, and differentiation. Only recently has it become clear how this single second messenger can simultaneously mediate so many processes. In current models of cyclic nucleotide signal transduction, cAMP acts locally within independently-regulated, spatially-restricted microdomains.

Cyclic AMP is produced from ATP by adenylyl cyclases (AC). Traditionally, cAMP had been thought to be produced exclusively via G protein-regulated, transmembrane adenylyl cyclases (tmACs) in response to hormones signaling via G protein coupled receptors (GPCRs). It is now known that mammalian cells contain a second type of AC, soluble adenylyl cyclase (sAC; ADCY10). sAC is a widely distributed source of cAMP, which unlike tmACs, is localized throughout the cell and targeted to intracellular compartments and cellular organelles, including inside the nucleus and the mitochondrial matrix. sAC is also distinct from tmACs in its regulation. It is considered that sAC is regulated by bicarbonate ($HCO_3^-$), rather than by heterotrimeric G proteins.

Pharmacologically, two sAC inhibitors useable in cellular systems have thus far been identified: catechol derivatives of estrogen (CEs) and KH7. CEs are natural products which were the first known inhibitors of sAC. While CEs have been useful for demonstrating sAC's role in cAMP dependent processes, CEs can also inhibit tmACs, which limits their utility. The second pharmacological sAC inhibitor, KH7, was identified in a small molecule screen against purified sAC protein. In contrast to CEs, KH7 is specific for sAC relative to tmACs, but its mechanism of action remains unknown, and it exhibits non-specific cellular effects.

SUMMARY OF THE DISCLOSURE

The present disclosure provides 6-amino substituted 2,6-diamino-4-chloropyrimidine compounds which are specific inhibitors of soluble adenylyl cyclase. 1. The compounds of the present disclosure may have the following structure:

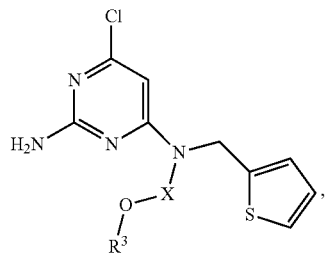

wherein
X is a substituted or unsubstituted $C_1$ to $C_3$ aliphatic group and $R^3$ is selected from the group consisting of:

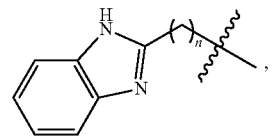

wherein n is 0 or 1, and

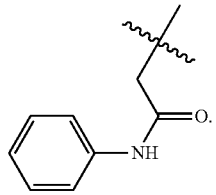 [SMILES: *CC(=O)Nc1ccccc1]

The compounds can be formulated with pharmaceutical carriers and used for reducing cyclic AMP levels. The compositions can be used for treatment of various conditions including ocular hypotony.

BRIEF DESCRIPTION OF THE DRAWINGS

For a fuller understanding of the nature and objects of the disclosure, reference should be made to the following detailed description taken in conjunction with the accompanying figures.

DETAILED DESCRIPTION OF THE DISCLOSURE

Figure 1:
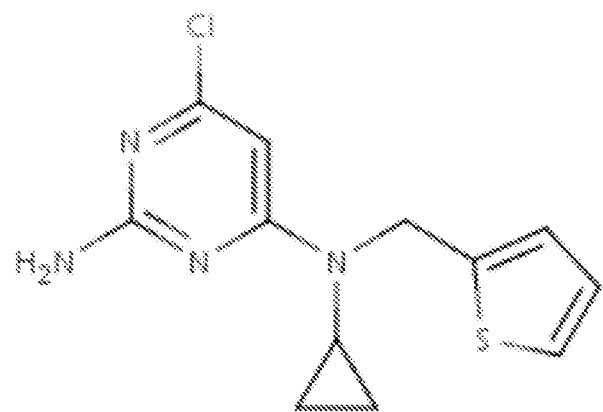
FIG. 1 shows the chemical structure of RU-0204277 (LRE1).

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

In an aspect, the present disclosure provides 6-amino substituted 2,6-diamino-4-chloropyrimidine compounds and compositions comprising one or more 6-amino substituted 2,6-diamino-4-chloropyrimidine compounds. The compounds are disubstituted at the 6 position of the amino group substituent of the pyrimidine ring.

The present disclosure also provides uses of such compounds and compositions. The compounds inhibit soluble adenylyl cyclase (sAC).

The compounds of the present disclosure have the following structure:

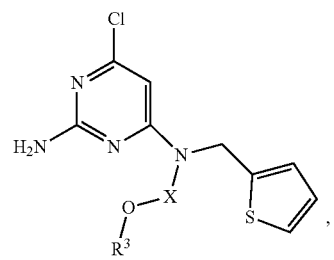

where X is a substituted or unsubstituted $C_1$ to $C_3$ aliphatic group and $R^3$ is selected from the group consisting of:

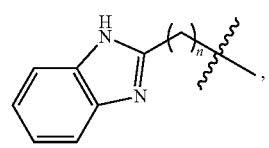

wherein n is 0 or 1, and

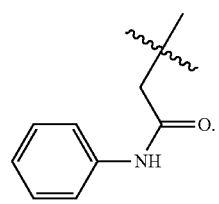 [SMILES: *CC(=O)Nc1ccccc1]

In an example, X is an unsubstituted $C_1$ to $C_3$ alkanediyl group having the following structure:

and m is 2 or 3.

In an example, X is an unsubstituted $C_1$ to $C_3$ aliphatic group having the following structure:

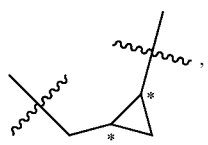

where *, individually at each occurrence, indicates R or S stereochemistry.

In various examples, the compound has the following structures:

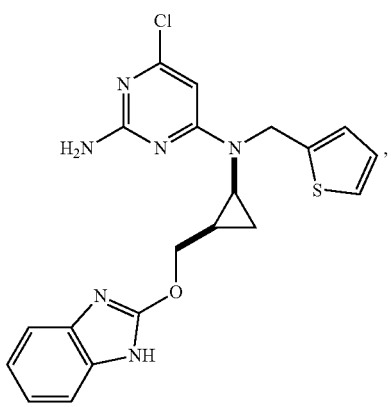

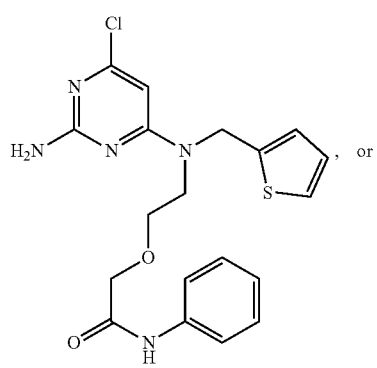

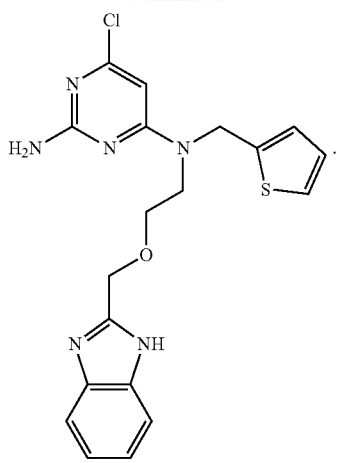

In an aspect, the present disclosure provides compositions comprising one or more sAC inhibitors of the present disclosure (e.g., comprising one or more compounds of the present disclosure and/or one or more sAC inhibitors identified in the present disclosure), in a pharmaceutically acceptable carrier.

In various examples, a composition is provided comprising one or more sAC inhibitors having the following structure:

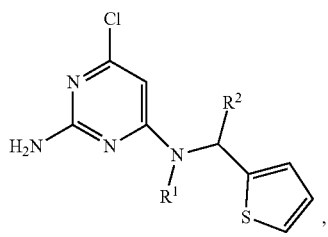

where $R^1$ is a substituted or unsubstituted $C_1$-$C_5$ aliphatic group, and $R^2$ is H or a substituted or unsubstituted phenyl group.

In an example, $R^2$ is a substituted phenyl group having the following structure:

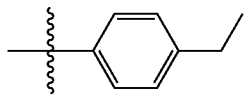

In an example, $R^1$ is a substituted $C_1$-$C_5$ alkanediyl group having one of the following structures:

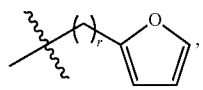

where r is 1, 2, 3, 4, or 5, or

where s is 1, 2, 3, 4, or 5.

In another example, $R^1$ is a substituted $C_1$-$C_5$ alkanediyl group having one of the following structures:

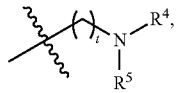

wherein t is 1, 2, 3, 4, or 5, and $R^4$ and $R^5$ are each independently a substituted or unsubstituted $C_1$-$C_5$ alkanediyl group.

In another example, $R^1$ is a substituted $C_1$-$C_5$ aliphatic group having the following structure:

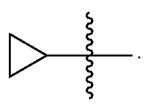

In various examples, the present composition comprises one or more of the following compounds:

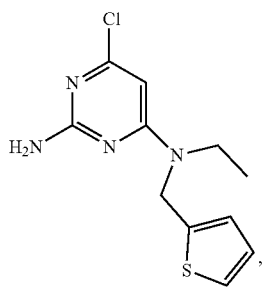

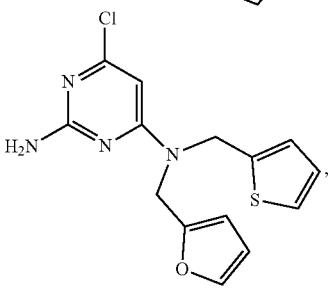

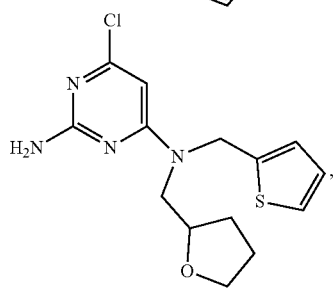

-continued

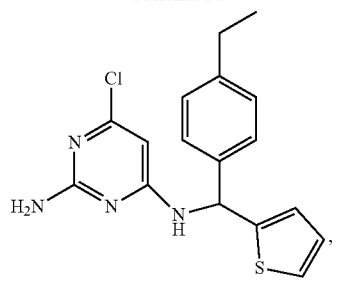

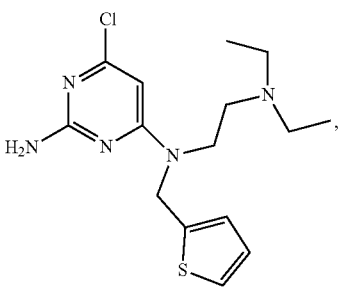

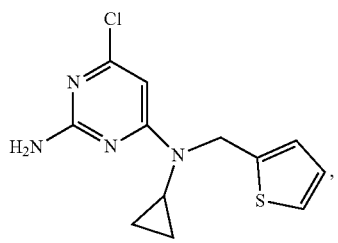

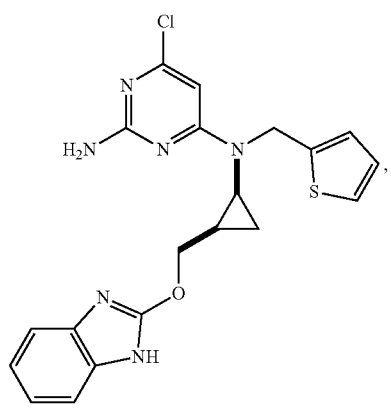

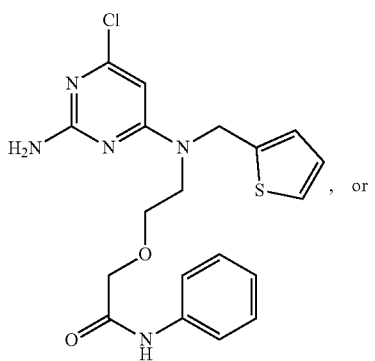, or

-continued

[Chemical structure: 4-chloro-2-amino-pyrimidine with N-substituent bearing thiophenylmethyl and ethoxymethyl-benzimidazole groups]

The present compounds may be delivered systemically or locally. For example, a pharmaceutical agent can be can be provided in combination with any suitable delivery form or vehicle, examples of which include, for example, liquids, caplets, capsules, tablets, inhalants or aerosol, etc. The delivery devices may comprise components that facilitate release of the pharmaceutical agents over certain time periods and/or intervals, and can include compositions that enhance delivery of the pharmaceuticals, such as nanoparticle, microsphere or liposome formulations, a variety of which are known in the art and are commercially available. Further, each composition described herein can comprise one or more pharmaceutical agents.

Pharmaceutically acceptable carriers may include a diluent, adjuvant, excipient, or other vehicle with which the therapeutic is administered. Some examples of materials which can serve as pharmaceutically-acceptable carriers include: sugars, such as lactose, glucose and sucrose; starches, such as corn starch and potato starch; cellulose, including sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other nontoxic compatible substances employed in pharmaceutical formulations. The composition, if desired, can also contain minor amounts of wetting or emulsifying agents, or pH buffering agents. Some examples of compositions suitable for mixing with the agent can be found in: Remington: The Science and Practice of Pharmacy (2005) 21st Edition, Philadelphia, Pa. Lippincott Williams & Wilkins. In one embodiment, the agent is substantially purified (e.g., substantially free from substances that limit its effect or produce undesired side-effects)

In one embodiment, the compositions are formulated for topical, transdermal, or mucosal use. Dosage forms for the topical, transdermal or mucosal administration include powders, sprays, ointments, pastes, creams, lotions, gels, solutions, patches and inhalants. In one embodiment, the composition may be formulated for parenteral, intravenous, or intramuscular delivery. These are typically aqueous compositions. Saline solutions and aqueous dextrose and glycerol solutions can also be employed as liquid carriers.

The components of the present disclosure may be mixed under sterile conditions with a pharmaceutically-acceptable carrier, and with any preservatives, buffers, or propellants which may be required. The ointments, pastes, creams and gels may contain additional excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Topical powders and sprays can also contain additional excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane. In one embodiment, transdermal patches may be used. These have the added advantage of providing controlled delivery to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel. In one embodiment, the compositions are applied to dermal patches, bandages, gauzes or other similar materials that can be directly applied to the affected area.

In one embodiment, the composition may be administered as an aerosol. This can be accomplished by preparing an aqueous aerosol, liposomal preparation or solid particles containing the active agents. A non-aqueous (e.g., fluorocarbon propellant) suspension could also be used. An aqueous aerosol may be made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), sorbitan esters, oleic acid, lecithin, such as glycine, buffers, salts, sugars or sugar alcohols. Aerosols generally are prepared from isotonic solutions. Sonic nebulizers may be used so as to minimize exposing the agent to shear, which can result in degradation of the compound.

For ophthalmic application, formulations may be prepared using a physiological saline solution. Other ophthalmically acceptable substances include sodium chloride, potassium chloride, sodium thiosulfate, sodium bisulfite and ammonium sulfate. Ophthalmic solutions can be maintained at a pH that is well tolerated in the eye. The formulations may also contain conventional, pharmaceutically acceptable preservatives, stabilizers and surfactants as described herein. Ophthalmic formulations may include preservatives, such as, for example, benzalkonium chloride, chlorobutanol, thimerosal, phenylmercuric acetate and phenylmercuric nitrate. Useful vehicles for ophthalmic preparations include, but are not limited to, polyvinyl alcohol, povidone, hydroxypropyl methyl cellulose, poloxamers, carboxymethyl cellulose, hydroxyethyl cellulose and purified water. Clarifying agents may be included for ophthalmic applications. Examples of ophthalmically-acceptable clarifying agents include, but are not limited to, polysorbate 20, polysorbate 80, and the like. Viscosity enhances may be included to increase the time of retention of the formulation in the eye, such as, for example, carboxymethylcellulose, carbomer (acrylic acid polymer), poly(methylmethacrylate), polyacrylamide, polycarbophil, acrylic acid/butyl acrylate copolymer, sodium alginate and dextran.

The compositions are administered in a therapeutically effect amount. It will be recognized by one skilled in the art that the form and character of the particular dosing regimen for the therapeutic agent of the present invention will be dictated at least in part by the route of administration and other well-known variables, taking into account such factors as the size, gender, health and age of the individual to be treated, and risk factors associated with cancer development for the individual, such as occupational, behavioral or family history related parameters. Based on such criteria, one skilled in the art can determine an effective amount of to administer to the individual.

The compositions may be delivered by any route. For example, the compositions may be delivered as topical formulation for application to mucosal surfaces. In one embodiment, the compositions may be delivered by routes other than topical or mucosal. For example, the compositions may be delivered via the digestive tract (as oral formulations) or via the circulatory system (intravenous, intramuscular, etc.) or directly to the relevant site.

In an aspect, the present disclosure provides methods of inhibiting soluble adenylyl cyclase (sAc). The method comprises contacting a cell in which inhibition of sAC is desired with a compound of the present disclosure or a composition of the present disclosure. The present compounds are specific in their inhibition of sAC, and do not appear to inhibit tmAC. On the contrary, a slight stimulatory effect on specific isoforms of tmACs was observed. Thus, the inhibitory effect on sAC is greater than an effect, if any, on tmAC.

Advantages of the present compounds over the known sAC selective inhibitor, KH7, include: the present compounds may be inhibit sAC to a greater extent than KH7 in cells, they may be more stable, they may not exhibit the off-target effects observed for KH7, and they may not exhibit the detergent sensitivity seen with KH7.

The present compounds and compositions can be used for treatment of various indications/conditions in an individual. For example, a sAC inhibitor would be useful as a hypotensive in the eye. The present compounds and compositions may be useful as a potential therapeutic for insulinemia. sAC inhibiting diminishes insulin release in insulinoma cell lines, in isolated islets, and in mice. The present compounds and compositions may also be useful for psoriasis. The present compounds can also be used as research reagents as sAC inhibitors.

Ophthalmic use of the present compounds and compositions includes treatment of ocular hypotony. Ocular hypotony (typically defined as TOP less than 5 mm Hg) is a rare, but potentially blinding condition for which there are no known therapeutic interventions. Another indication where the present compounds and compositions may be used is in the reversal of overcorrection of ocular hypertensive conditions, such as glaucoma. Glaucoma is a potentially blinding condition in which optic nerve injury occurs due to elevated intraocular pressure (IOP). Current treatment strategies for treatment of glaucoma are directed to reducing TOP, either by pharmacologically reducing the rate of aqueous flow from ciliary bodies or by surgically enhancing drainage through the trabecular meshwork (trabeculectomy). However, surgical treatment to relieve intraocular pressure can sometimes result in very low intraocular pressure (i.e., ocular hypotony). Use of trabeculectomy is limited by the fact that many glaucoma patients suffer visual disability from ocular hypotony as a surgical complication. Hypotonic maculopathy has been reported in up to 20% of trabeculectomies and can result in permanent visual impairment. The present compositions may be administered during the period of ocular hypotony. The availability of a therapeutic approach to ocular hypotony may aid in developing aggressive surgical treatments of glaucoma.

Ocular hypotony may also occur in eyes with uveitis, as a complication of other eye surgeries, for unknown reasons. In severe cases, hypotony leads to phthisis bulbi (shrunken, non functional eyes). There are currently no FDA approved therapies for the reversal of ocular hypotony, nor are there any suitable or reliable off-label therapies to elevate IOP. The present compounds and compostions can be used for administration to an individual for the treatment of any condition involving ocular hypotony.

The administration of the present compositions, such as for ophthalmic use, can be carried out in conjunction with measurement and monitoring of TOP. For example, TOP can be monitored at regular intervals following glaucoma surgery or other procedures, and if IOP falls below 5 mm Hg, the present composition can be administered so as to restore the IOP to normal levels. The dose and frequency of administration can be adjusted so that TOP is maintained within normal levels.

In one embodiment, the present compounds or compositions can be used for increasing intraocular pressure in an individual who is exhibiting ocular hypotony or who is suspected of developing ocular hypotony comprising administering to the individual a therapeutically effective amount of a composition comprising one or more compounds described herein. The individual may be an individual who has undergone surgical treatment for glaucoma and needs IOP restored to normal levels.

The compounds and compositions of the present disclosure inhibit soluble sAC. The compounds and compositions of the present disclosure inhibit soluble sAC in a cell. In one embodiment, the present compounds and compositions inhibit at least 90% of the in vitro activity of sAC. In an example, a method of inhibiting soluble adenyl cyclase in a cell comprises contacting the cell with a compound of the present disclosure or a composition of the present disclosure.

The following examples are presented to illustrate the present disclosure. They are not intended to limiting in any matter.

Example 1

This example provides a description of examples of compounds of the present disclosure and uses thereof.

Results

Development of a novel high-throughput adenylyl cyclase assay and its use to screen a library for sAC inhibitors. We have a validated and confirmed hit from our small molecule screen for inhibitors of the HTSRC high diversity library. RU-0204277 (FIG. 1). We obtained powder from a commercial supplier, and we confirmed the compound inhibited sAC in the two-column, radioactivity cyclase assay in our laboratory. We also demonstrated that the compound is efficacious in cellular systems, and appears to be selective for sAC relative to tmACs. And finally, we have co-crystals with sAC which show the compound binding to and occupying the bicarbonate binding site.

Figure 2:
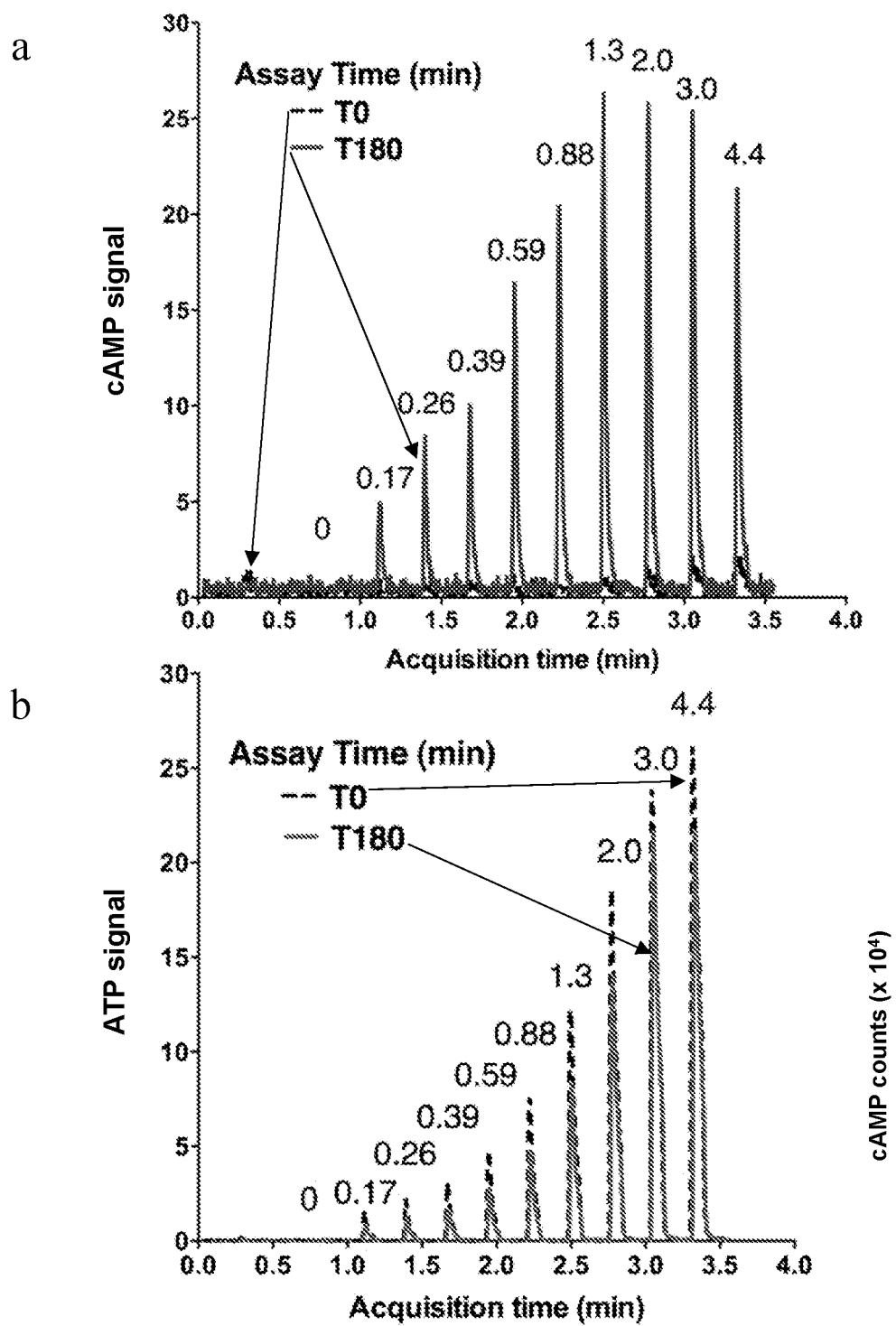
FIG. 2 shows validation of RapidFire Mass Spectrometry System (RF-MSS) cyclase assay and high throughput screening conditions. (a) Detection of cAMP formation and (b) ATP consumption using RF-MSS. An example of a RF-MS chromatogram showing (a) the product cAMP, as extracted ion intensity (EIC: MW 328.0412)×$10^3$, and (b) substrate ATP, as extracted ion intensity (EIC: MW 505.9816)×$10^4$. The order of peaks derives from increasing input ATP, shown numerically (in mM) on top of each peak. Peaks recorded at time "0" and after incubation with sAC for 180 min. (c) sAC kinetics using RF-MSS. Human sAC activity was measured as a function of substrate of ATP-$Mg^{2+}$ for 120 min in the presence of excess $MgCl_2$ (20 mM). Shown are curves for $Mg^{2+}$ alone (dots), $Mg^{2+}$ plus 40 mM $HCO_3^-$ (squares), $Mg^{2+}$ plus 10 mM $Ca^{2+}$ (triangles, ▲), and $Mg^{2+}$ plus 40 mM $HCO_3^-$ and 10 mM $Ca^{2+}$ (inverted triangles, ▼). All determinations are representative of at least two independent experiments and the curves are non-linear fits generated by Prism (Graphpad). (d-f) Validation of RF-MSS high throughput screen assaying human sAC in the presence of 1 mM ATP, 5 mM $MgCl_2$, 5 mM $CaCl_2$, and 40 mM $NaHCO_3$. (d) Comparison of active (dots) and denatured (open squares) sAC enzyme leads to Z' score of 0.7. (e) Pilot screen using the 1280 compound LOPAC library of pharmacologically active compounds (dots); DMSO control (squares); denatured sAC protein (triangles). (f) To assess the reproducibility of the RF-MSS high throughput screen, the LOPAC library was tested twice. LOPAC compounds (dots); DMSO control (square); denatured sAC protein (red dots). The correlation of the results on separate days is shown ($R^2$=0.81).
Figure 2:
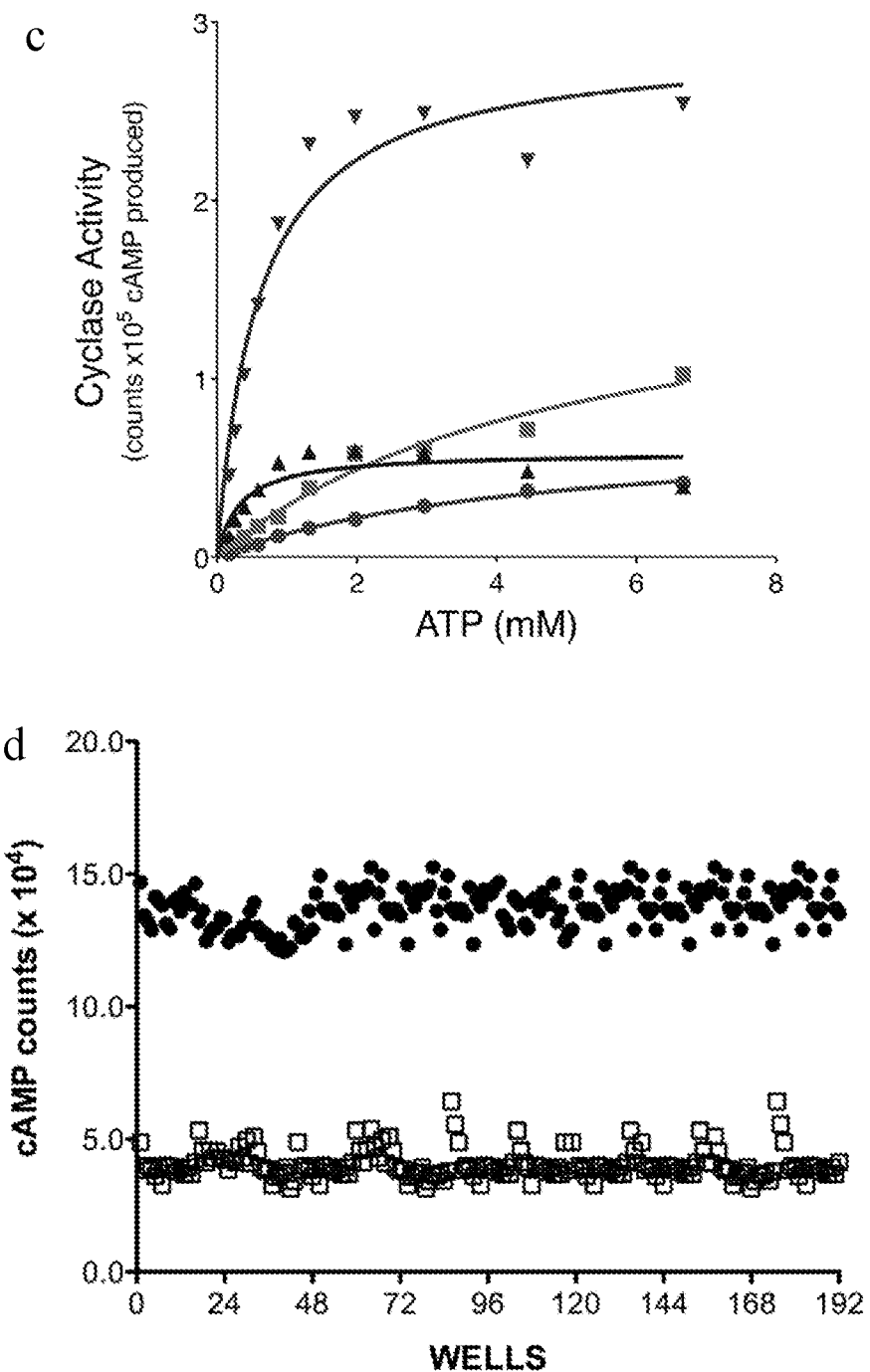
Figure 2:
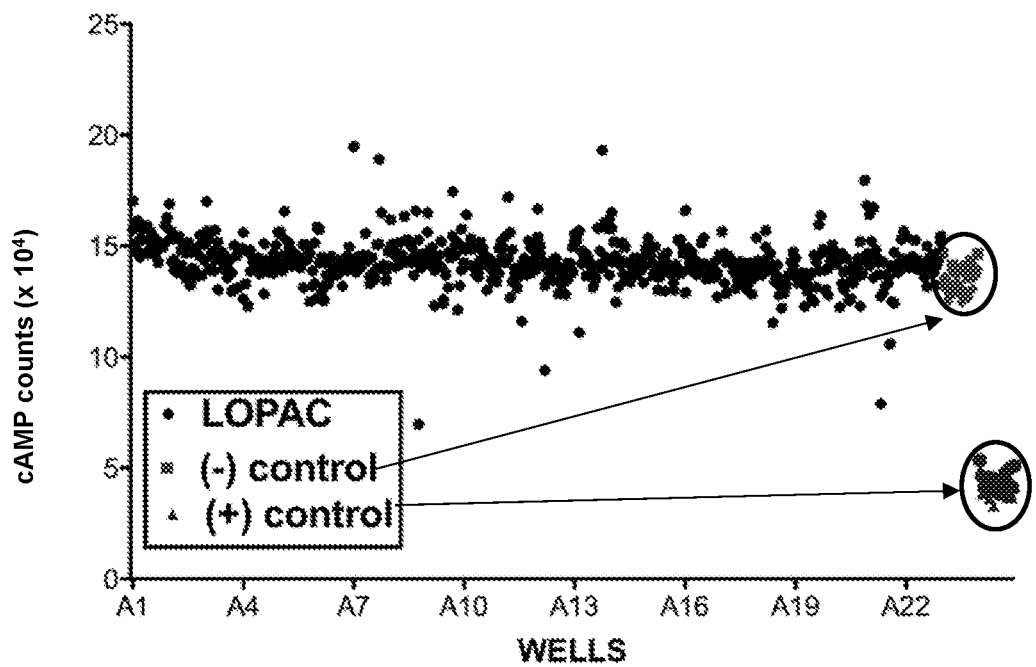
Figure 2:
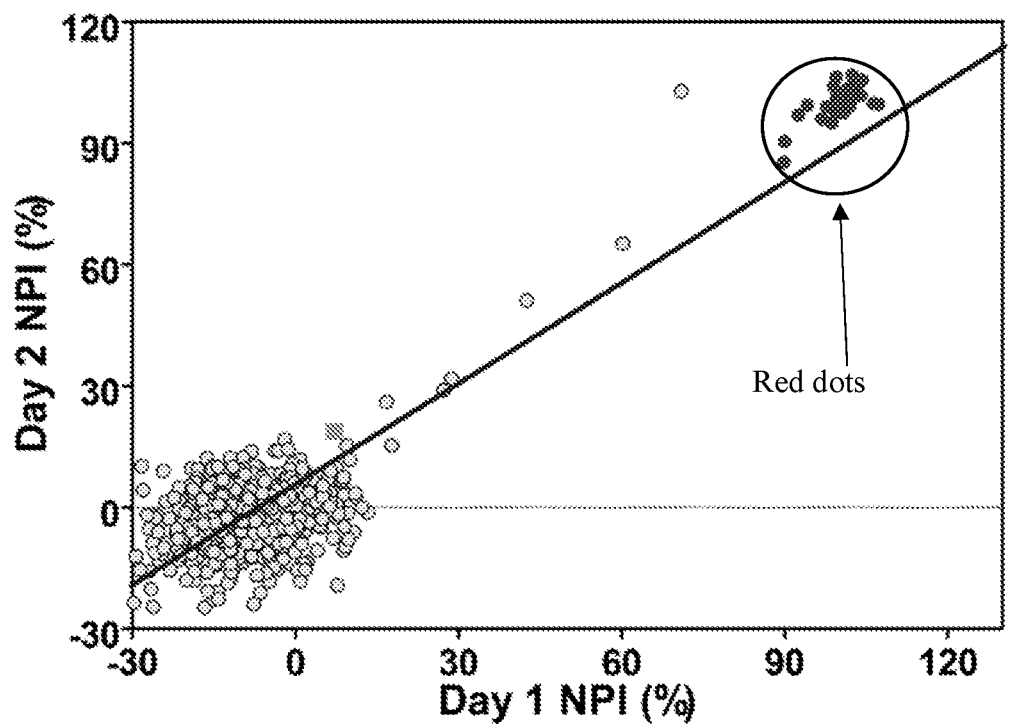

We developed a mass spectrometry (MS) based assay that accurately quantifies levels of both product cAMP and substrate ATP in a single sample over several orders of magnitude. Thus, by correlating cAMP production (FIG. 2A) with reduction of input ATP (FIG. 2B), this MS-based assay provides assurance that the measured product derives from substrate similar to traditional, radioactivity-based assays where [$\alpha^{32}$P] ATP is converted into [$^{32}$P] cAMP. The RapidFire 365 High-throughput MS System (Agilent Technologies; RF-MSS) can process samples every 15 seconds allowing analysis of a 384 well plate in under two hours; thus, RF-MSS provides a platform for high throughput MS screening which can simultaneously measure both cAMP produced and ATP consumed in an individual sAC assay. Using the RF-MSS we observed no appreciable sample carryover between assay samples, and we were able to detect both a sAC-dependent increase in cAMP signal (FIG. 2A) and decrease in ATP signal (FIG. 2B) over time. When measured in the presence of increasing concentrations of substrate ATP in the presence of $Mg^{2+}$ as the sole divalent cation, $HCO_3^-$ stimulated sAC activity by increasing the $V_{max}$ with little effect on the apparent $K_m$ for substrate ATP-$Mg^{2+}$ (FIG. 2C). Addition of $Ca^{2+}$ stimulated sAC activity by decreasing its apparent $K_m$ for ATP, and addition of both $Ca^{2+}$ and $HCO_3^-$ synergistically activated sAC. These data confirm that using RF-MSS as a tool for measuring in vitro adenylyl cyclase activity is comparable to the known, radioactivity based, "two-column" method for measuring adenylyl cyclase activity.

For screening, we chose in vitro assay conditions which reflect physiologically stimulated enzyme (i.e., in the presence of $Mg^{2+}$, $Ca^{2+}$, and $HCO_3^-$) to maximize our chances for identifying therapeutically useful sAC inhibitors. Under these conditions, the cAMP generated in the presence of active human sAC protein compared to the RF-MSS signal for cAMP in the presence of inactive sAC yields a Z' score of ~0.7 (FIG. 2D). Thus, to screen for inhibitors, we used denatured sAC protein as "positive control." Under these conditions, a pilot screen of the LOPAC reference library (Sigma) containing small organic compounds with well-documented pharmacological activities also yielded a Z' factor of ~0.7 (FIG. 2E). Repeated screening of individual plates of the LOPAC library confirmed reproducibility with an $R^2$ value of 0.81 (FIG. 2F).

Figure 3:
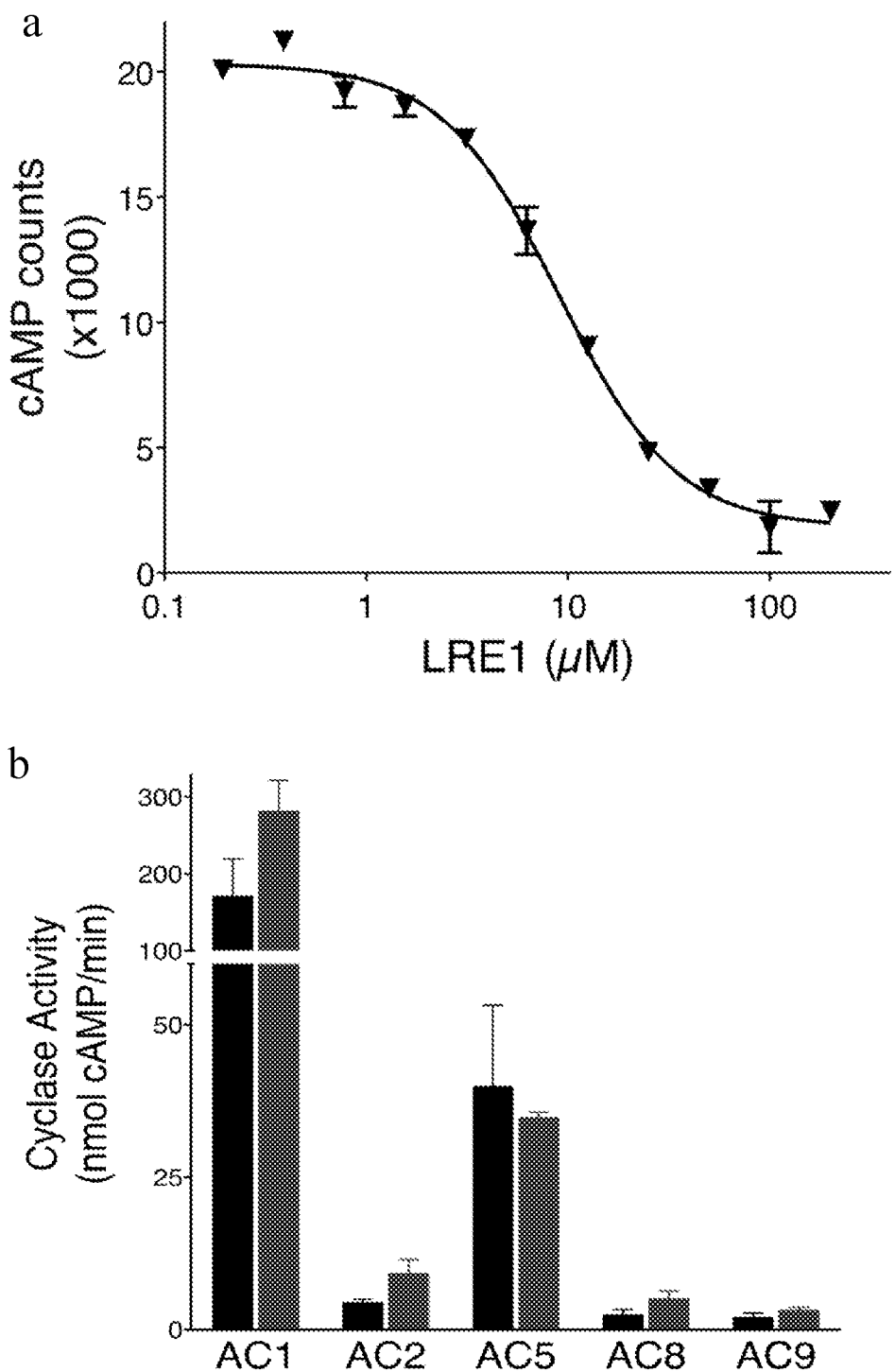
FIG. 3 shows LRE1 is a potent and selective inhibitor of sAC in vitro and in cells. (a) Concentration-response curve of LRE1 on sAC protein in the presence of 1 mM ATP, 5 mM $MgCl_2$, 5 mM $CaCl_2$, and 40 mM $NaHCO_3$ measured by RF-MSS. Values are averages of triplicate determinations with S.E.M. indicated. (b) Adenylyl cyclase activities of whole extracts of 293 cells heterologously expressing tmAC Types I (AC1), II (AC2), V (AC5), VIII (AC8), and IX (AC9) in the presence of 100 µM GTPγS alone (left bar in each series) or in the presence of 50 µM LRE1 (right bar in each series). Shown are activities of tmAC expressing extracts after the activity of empty vector transfected lysate was subtracted. The activity in vector transfected HEK293 lysates in the presence of 100 µM GTPγS alone was 5.5±0.8 nmol cAMP/min; its activity in the presence of 100 µM GTPγS+50 µM LRE1 was 7.7±1.7 nmol cAMP/min. Shown is a representative assay repeated at least three times; values represent averages of quintuple determinations with S.E.M. (c-e) Cellular cAMP accumulation measured by ELISA-based Correlate EIA cAMP assay. (c) Concentration-response of LRE1 (squares) and KH7 (circles) on sAC overexpressing 4-4 cells. (d) Concentration-response of LRE1 on forskolin-stimulated sAC knockout fibroblasts. Panels B and C show representative assays repeated at least three times; values are means+/−S.E.M. of triplicate determinations normalized to activity in the absence of any compound. (e) Concentration-response of LRE1 on glucose-induced cAMP production in INS-1E cells. After a 2 hour starvation in 2.5 mM glucose, media was replaced with either 2.5 mM glucose (Low glucose, left bars) or 16 mM glucose (High glucose, right bars) in the presence of 500 µM IBMX and 0 (first bar from the left in each series), 10 µM (second bar from the left in each series), 30 µM (third bar from left in each series), 50 µM (fourth bar from the left in each series), or 100 µM (fifth bar from the left in each series) LRE1. Accumulated cAMP was quantitated after 10 minutes; data are presented as pmol cAMP accumulated per $2.5 \times 10^5$ cells. All assays are reported as the mean+/−S.E.M. of triplicate determinations of at least three independent experiments. (f) The glucose-induced cAMP, calculated from panel (e) by subtracting the cAMP accumulated in low glucose from the cAMP accumulated in high glucose, in the presence of the indicated concentration of LRE1.
Figure 3:
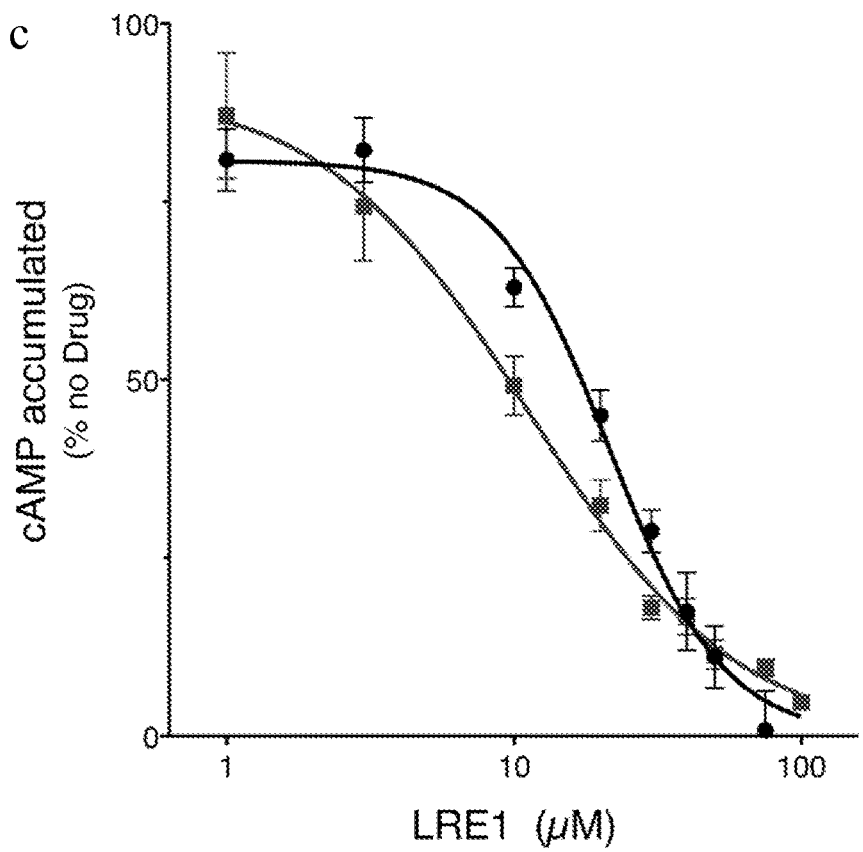
Figure 3:
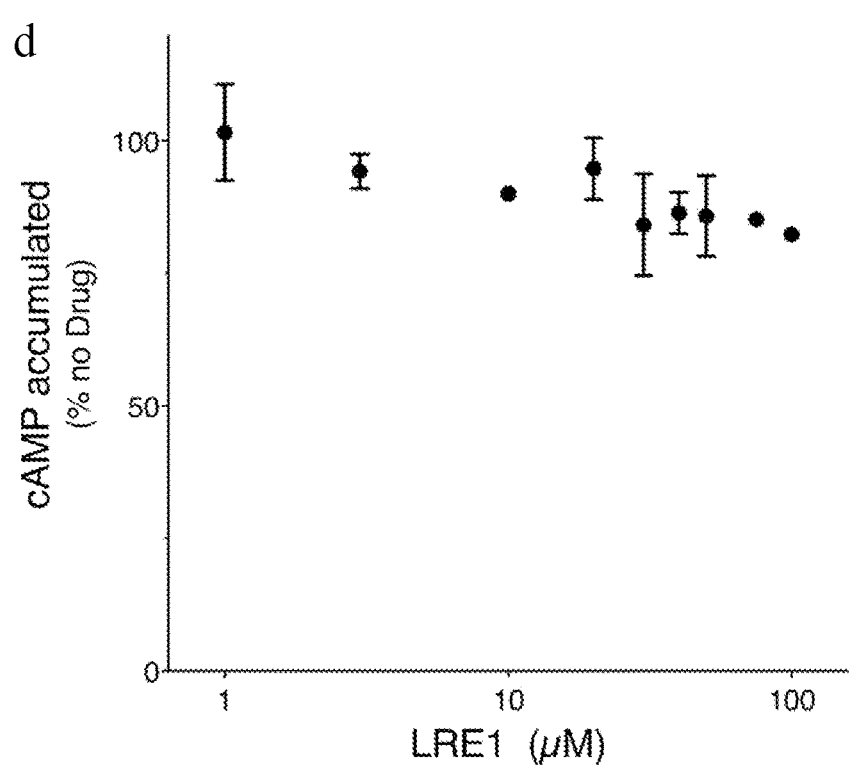
Figure 3:
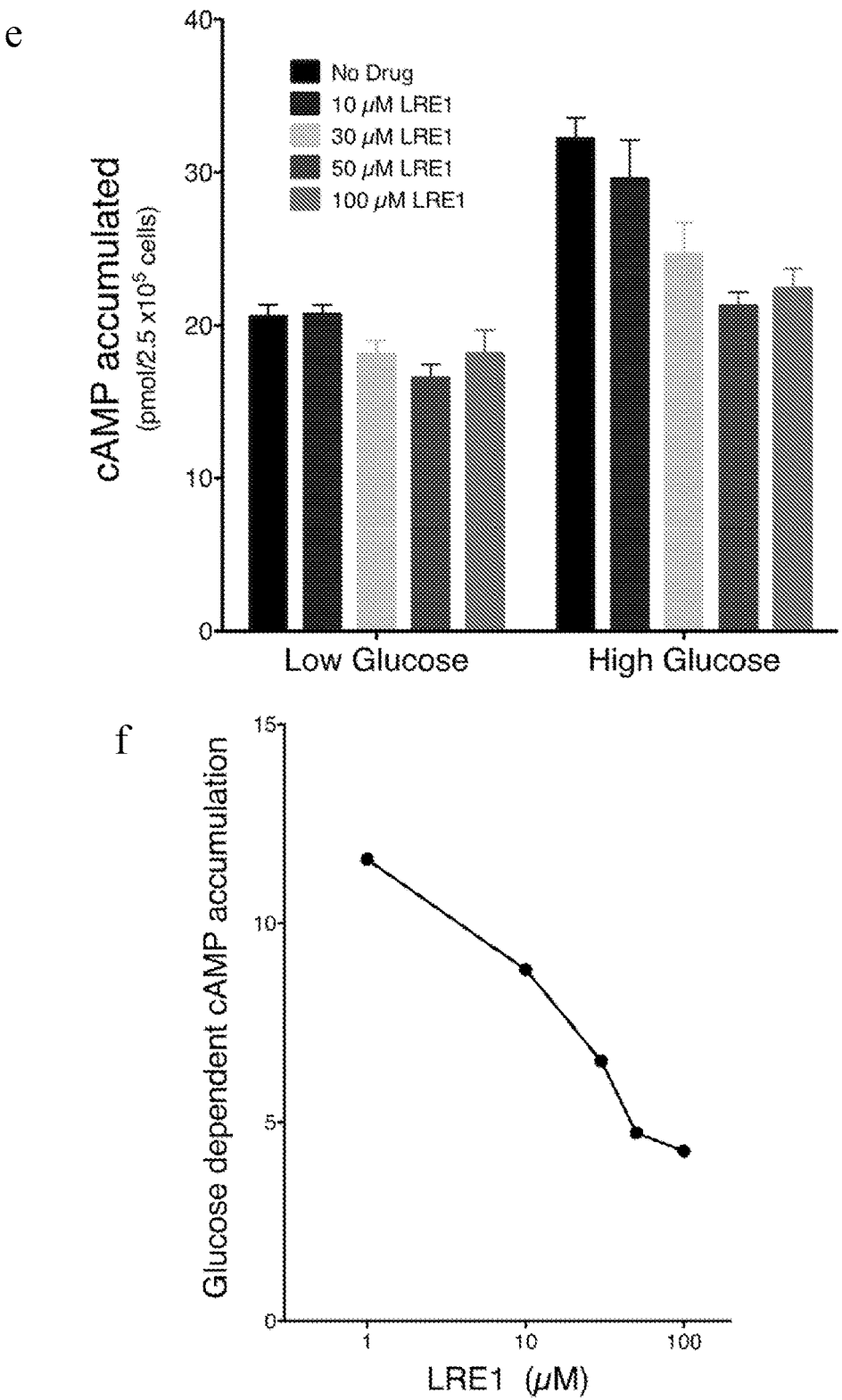

A total of 33,135 compounds, selected (as described in Methods) from a larger set of 7.87 million commercially available screening compounds to maximize coverage of chemical space and "drug-likeness" properties, were screened at 10 μM for their ability to inhibit in vitro human sAC activity. From the 33,135 compounds screened, 46 compounds which inhibited sAC activity by ≥35% (0.14% hit rate) were tested for reproducibility and concentration-dependency. To avoid assay dependent artifacts, reproducibility and concentration-dependency were simultaneously assessed in the RF-MSS cyclase assay as well as in an independent colorimetric competitive enzyme immunoassay (i.e., ELISA-based Correlate-EIA Direct cAMP Assay). Four (4) of the 46 compounds proved to be concentration-dependent sAC inhibitors in both types of assay (Table 1). Two compounds, RU-0207148 and RU-0204277, reproducibly had $IC_{50}$s in the low μM range, which is comparable to KH7. We decided to focus on RU-0204277 due to its lower molecular weight, better Q.E.D. score, and unique structural features relative to KH7. The systematic name of RU-0204277 is 6-chloro-N4-cyclopropyl-N4-[(thiophen-3-yl)methyl]pyrimidine-2,4-diamine; hereafter, we refer to it as LRE1. The purity and identity of the "cherry picked" compounds were confirmed by LC-MS, and both commercially obtained LRE1 and independently synthesized LRE1 inhibited sAC in vitro activity with similar potency as the "cherry picked" compound. The concentration-response of independently synthesized LRE1 on sAC protein is shown in FIG. 3A.

TABLE 1

| Molecule Name | Structure | MW (g/mol) | Primary Screen (% NPI) | RF-MSS Assay $IC_{50}$ (μM) | EIA Assay $IC_{50}$ (μM) |
|---|---|---|---|---|---|
| RU-0204277-LRE1 (0.872) | 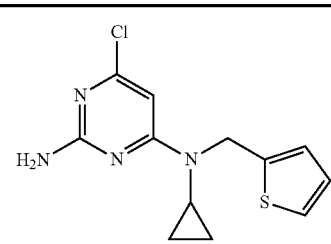 | 280.8 | 57.0 | 3.3 | 6.3 |
| RU-0207148 (0.752) | 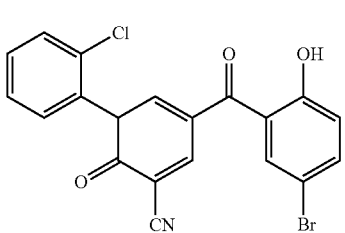 [SMILES: N#CC1=CC(C(=O)c2cc(Br)ccc2O)=CC(c2ccccc2Cl)C1=O] | 429.7 | 67.6 | 5.7 | 4.4 |

TABLE 1-continued

| Molecule Name | Structure | MW (g/mol) | Primary Screen (% NPI) | RF-MSS Assay IC$_{50}$ (μM) | EIA Assay IC$_{50}$ (μM) |
|---|---|---|---|---|---|
| RU-0207328 (0.534) | 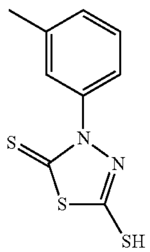 | 240.7 | 58.1 | >20 | >20 |
| RU-0206544 (0.707) | 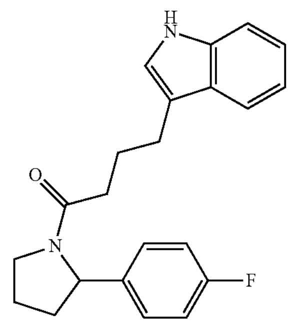 [SMILES: O=C(CCCc1c[nH]c2ccccc12)N1CCCC1c1ccc(F)cc1] | 350.4 | 50.0 | >20 | >20 |
| KH7 | 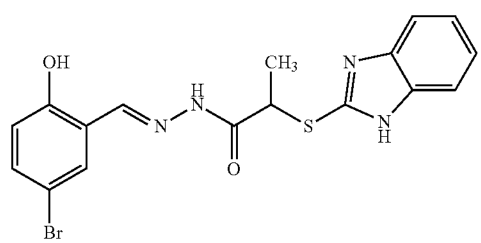 [SMILES: CC(Sc1nc2ccccc2[nH]1)C(=O)N/N=C/c1cc(Br)ccc1O] | 419.3 | — | — | 8.0* |

*See Wu et al., *Nat. Neurosci.*, 9, 1257-1264 (2006).

LRE1 is specific for sAC.

LRE1 is not a "frequent hitter," it was negative in 17 other in vitro and cell-based screens against various targets including other nucleotidyl cyclases, proteases, ion channels, and at least one GPCR. In mammals, the enzymes most related to sAC are the G protein-regulated transmembrane adenylyl cyclases (tmACs). Nine genes encode tmAC isozymes in mammals, but among these, tmACs I, III, and VIII define a highly homologous and biochemically related subclass; tmACs II, IV, and VII define a second subclass; and tmACs V and VI define a third. Therefore, to assess LRE1's selectivity for sAC relative to other mammalian adenylyl cyclases, we tested whether LRE1 affected the in vitro G protein stimulated activities of heterologously expressed tmACs I, II, V, VIII, and IX. At 50 μM, which completely inhibited sAC, LRE1 did not inhibit any tmAC (FIG. 3B).

LRE1 is efficacious in cellular systems.

We next tested whether LRE1 could inhibit sAC in intact cells. Cellular levels of cAMP reflect a balance between its synthesis by adenylyl cyclases and its catabolism by phosphodiesterases (PDEs). When cells are grown in the presence of a cocktail of PDE inhibitors, they accumulate cAMP which reflects the activity of endogenous adenylyl cyclases. To assess adenylyl cyclase inhibitor efficacy in cellular systems, we used 4-4 cells, which stably overexpress sAC in a HEK293 cell background. The cAMP accumulation in 4-4 cells in the presence of PDE inhibitors is almost exclusively due to sAC. LRE1 inhibited cAMP accumulation in 4-4 cells with an IC$_{50}$ of 11 μM (FIG. 3C), which is comparable to KH7 and which is in good agreement with LRE1's≤10 μM IC$_{50}$ on sAC protein (FIG. 3A and Table 1).

To confirm LRE1's specificity for sAC relative to tmACs in a cellular context, we used a second cell line, immortalized mouse embryo fibroblasts derived from sAC knockout mice (sAC KO MEFs). sAC KO MEFs are devoid of sAC, and they express a mixture of tmAC isoforms, specifically tmAC Types I, III, IV, VI, VII, VIII, and IX[41]. LRE1 was inert towards forskolin-stimulated cAMP accumulation in sAC KO MEFs (FIG. 3D). Together, these assays identify LRE1 as a sAC-specific inhibitor suitable for use in cell-based assays.

We demonstrated LRE1's ability to inhibit a physiological sAC-dependent cAMP response. Pancreatic β cells sense serum glucose and respond to elevated glucose levels by releasing insulin. sAC is known to be essential for glucose sensing and for glucose dependent insulin secretion. INS-1E cells are an insulinoma cell line which recapitulate β cell glucose sensing, and we previously showed that while tmACs are largely responsible for the basal cAMP production in INS-1E cells growing in low glucose, sAC is responsible for the increased cAMP production in cells grown in high glucose. Consistent with it being a sAC specific inhibitor, LRE1 effectively blocks the glucose induced cAMP response in INS-1E cells, while having little effect on the basal, tmAC-dependent cAMP synthesized in low glucose (FIG. 3E,F).

LRE1 allosterically inhibits sAC by binding to the bicarbonate activation site

Figure 4:
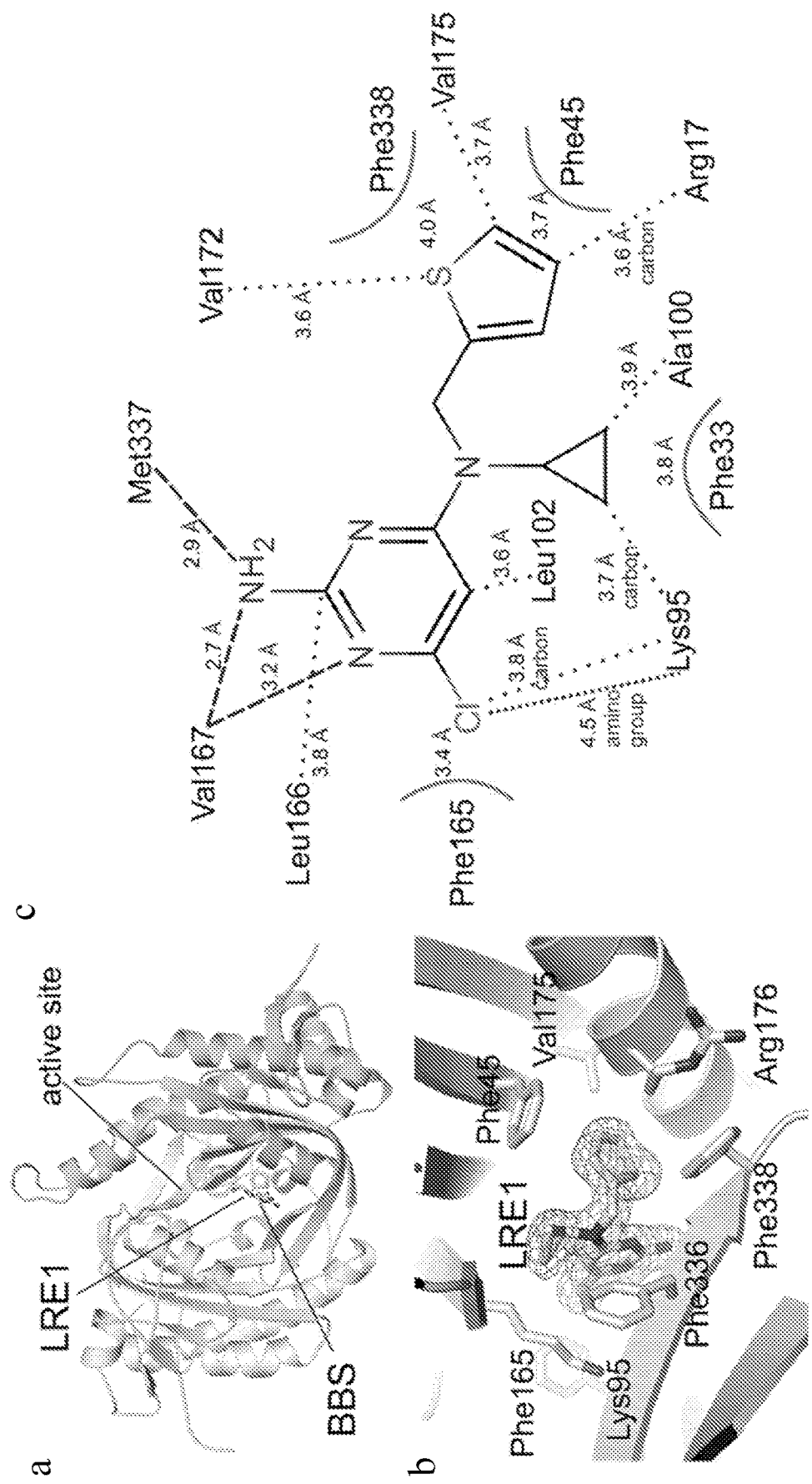
FIG. 4 shows structural and mechanistic characterization of sAC inhibition by LRE1. (a) Overall structure of the sAC/LRE1 complex, with $C_1$ and $C_2$. LRE1 is shown in stick representation, and active site and BBS are indicated. (b) Close-up of the BBS with ligand and interacting residues as sticks colored according to atom type. LRE1 is overlaid with $2F_o$-$F_c$ electron density contoured at 1σ. (c) Interaction scheme for sAC and LRE1. Interactions of side chains are indicated by black dots and by arcs for aromatic residues, and backbone interactions by dashed lines. (d) sAC activity, measured by RF-MSS in the presence of the indicated concentration of LRE1 and 1 mM ATP, 5 mM $MgCl_2$, 5 mM $CaCl_2$, with 0 $NaHCO_3$ (dots); 10 mM $NaHCO_3$ (squares); 20 mM $NaHCO_3$ (triangles); or 80 mM $NaHCO_3$ (diamonds). Data represent means±S.E.M. of triplicate determinations of an experiment repeated twice. (e) Overlay of sAC/LRE1 with a sAC/bicarbonate complex (RMSD 0.3 Å$^2$ for 352 $C_\alpha$ atoms). The ligands and the two key residues for bicarbonate binding are shown as sticks colored according to atom type. (f) sAC activity, measured by RF-MSS in the presence of the indicated concentration of LRE1 and either 0.6 mM ATP (diamonds), 0.9 mM ATP (triangles), 1.3 mM ATP (squares), or 2.0 mM ATP (dots) and 5 mM $MgCl_2$, 5 mM $CaCl_2$, with 40 mM $NaHCO_3$. Data represent individual points of a serial dilution of an experiment repeated three times. (g) Crystal structure of a sAC/ApCpp/LRE1 complex. The substrate analog ApCpp in the active site and the inhibitor in the BBS are shown as sticks colored according to atom type and overlaid with $2F_o$-$F_c$ electron density contoured at 1σ. $Ca^{2+}$ is shown as sphere. (h) Overlay of sAC/ApCpp/LRE1 with a sAC/ApCpp complex (RMSD 0.31 Å$^2$ for $C_\alpha$ atoms). Ligands and key interacting residues are shown as sticks, and $Ca^{2+}$ as a sphere.
Figure 4:
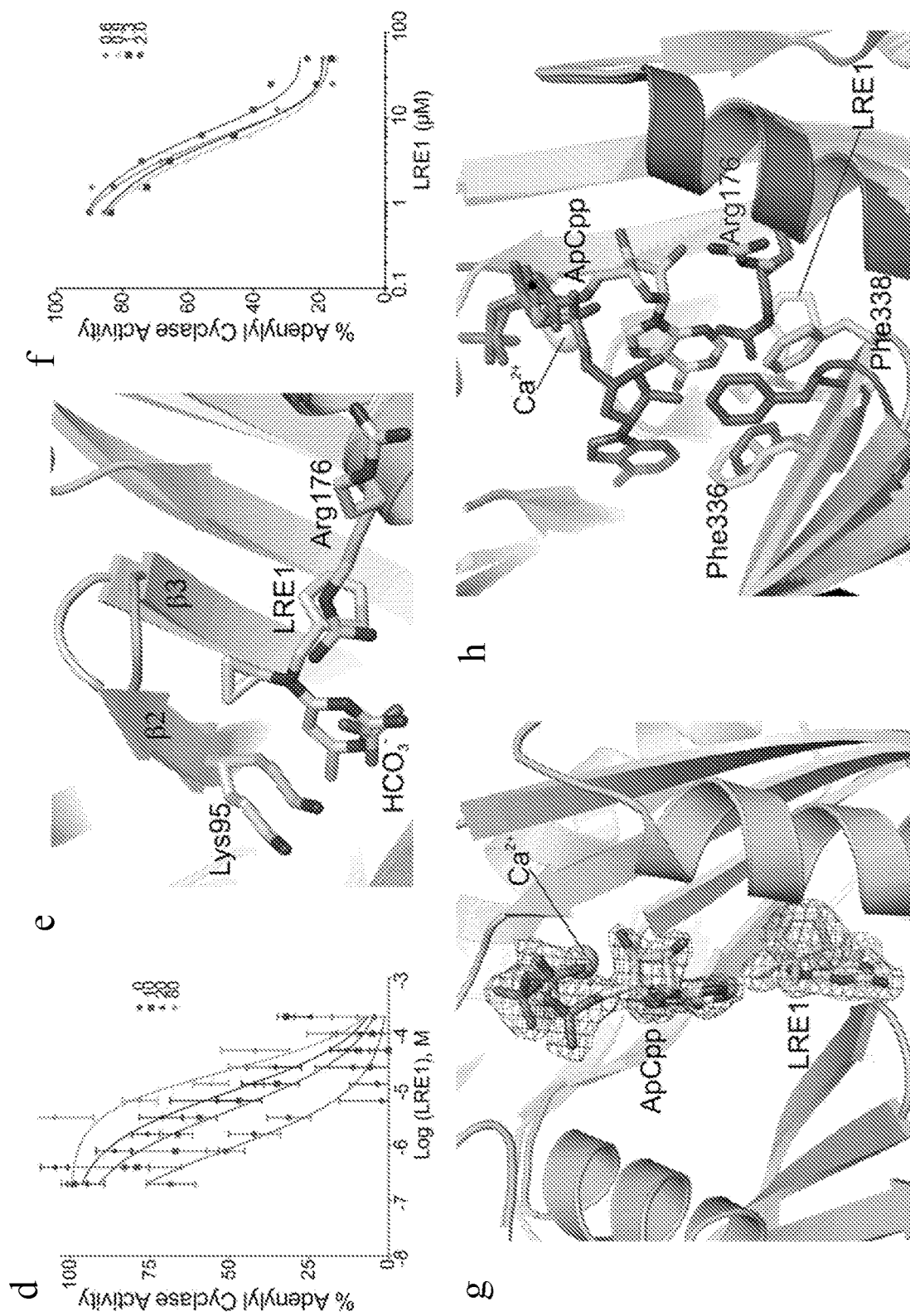

To obtain molecular insights into the LRE1 binding site and inhibition mechanism, we solved the crystal structure of a sAC/LRE1 complex. LRE1 was soaked into sAC-cat apo crystals, and excellent additional electron density for the LRE1 ligand was visible after molecular replacement phasing of the 1.79 Å resolution diffraction data (Table 1). The final sAC/LRE1 complex showed good refinement statistics ($R/R_{free}$=16.1/20.3%) and a ligand geometry well-defined by electron density (FIG. 4A,B; 7A). LRE1 occupies the $HCO_3^-$ binding site (BBS) between Lys95 and Arg176, both of which are essential for $HCO_3^-$ regulation. The inhibitor extends into a channel connecting the BBS to the active site (see below). The overall B-value of 20.7 Å$^2$ for LRE1 corresponds to the B-values of its protein environment and indicates a tightly bound ligand. The substituted pyrimidine ring of LRE1 occupies a rather hydrophobic pocket formed by Phe165, Leu166, Leu102, Val167, Met337 and Lys95 (FIG. 4B,C). Hydrogen bonds are formed by the backbone oxygens of Val167 (2.7 Å) and Met337 (2.9 Å) to the amino group of the LRE1 pyrimidine, and by the Val167 α-amino group to a ring nitrogen. The chlorine substituent points into a highly hydrophobic pocket formed by Leu102, Val167, Phe165, Leu166, and the side chain carbons of Lys95, and it might for a weak dipole-charge interaction with the Lys95 amino group. The LRE1 cyclopropene ring is accommodated in a hydrophobic pocket lined by Phe336 and Phe45/Ala97. Phe45 also interacts, through a T-shaped it-stacking interaction, with the LRE1 thiophene ring, which is further surrounded by Val175/172, Phe338, and Arg176. This Arg is a "trigger arm," which links BBS and substrate binding site. In the LRE1 complex, the Arg176 side chain is in a unique orientation; it points away from active site and BBS and is fixed in this orientation through polar interactions with Asp339 and Asn180.

Consistent with LRE1 occupying the allosteric regulatory region mediating $HCO_3^-$-dependent sAC activation, kinetic experiments revealed that LRE1 inhibition is competitive with $HCO_3^-$ (FIG. 4D). Overlaying the sAC/LRE1 complex with a sAC complex in the presence of $HCO_3^-$ (PDB code 4c11) shows that part of the LRE1 pyrimidine ring assumes the positions of the $HCO_3^-$ atoms (FIG. 4E) and appears to simulate their polarity pattern. However, the bulky LRE1 is not compatible with the Arg176 conformation assumed to be relevant for sAC activation. For its interaction with the LRE1 thiophene, Phe338 from the β2-β3 loop is pulled ~3 Å toward the thiophene pocket, away from its normal position next to the active site. The LRE1 thiophene itself and the rearranged Phe338 block the region accommodating Arg176 during $HCO_3^-$ binding. Due to the size of LRE1, Lys95, which forms the BBS border opposite from Arg176, is also shifted ~2.1 Å away from its normal position. These distortions explain why occupying the BBS with LRE1 does not stimulate sAC activity.

Figure 7:
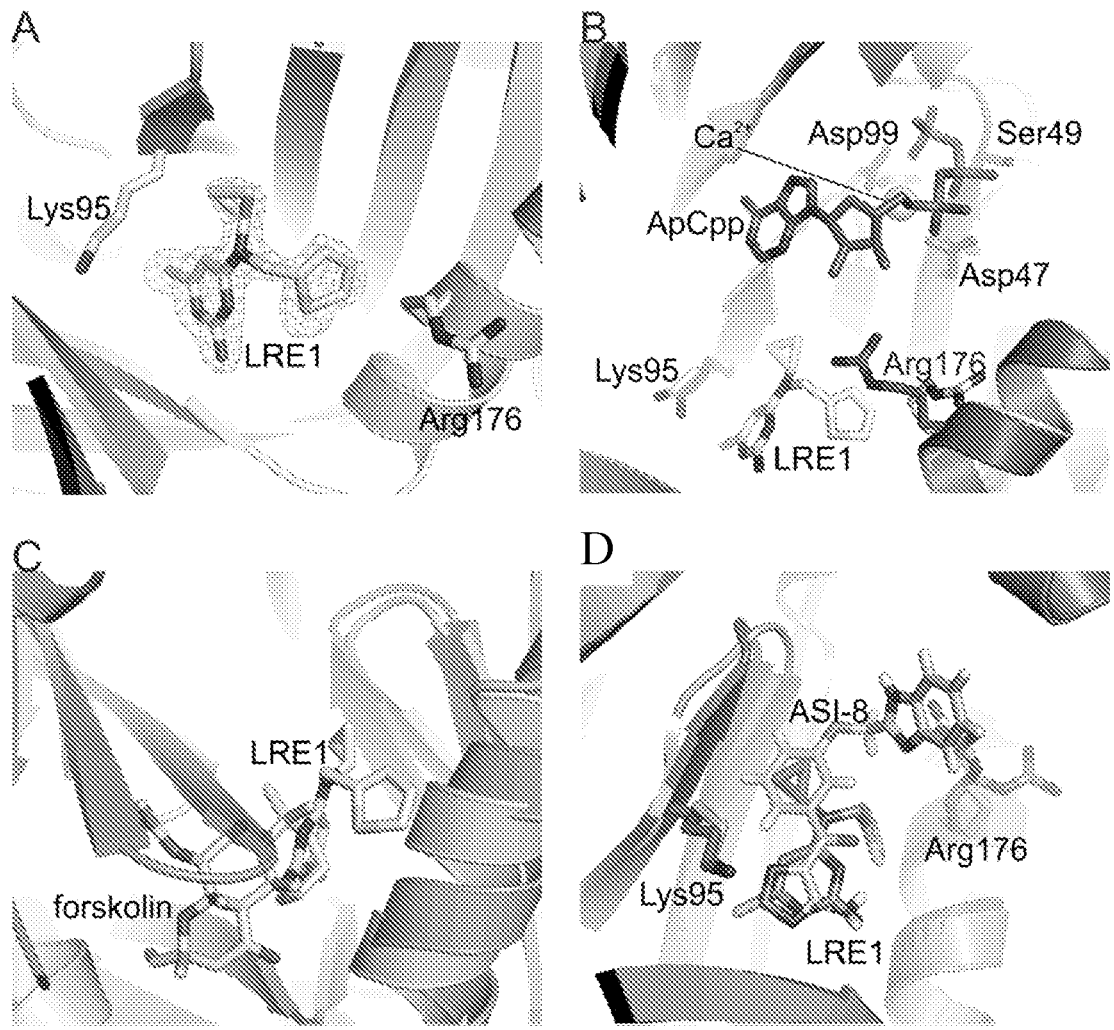
FIG. 7 shows structural analysis of sAC inhibition by LRE1 and comparison to other AC modulators. (A) Close-up of the BBS of the sAC/LRE1 complex. Ligand and key interacting residues are shown as sticks colored according to atom type. LRE1 is overlaid with $F_o$-$F_c$ omit electron density contoured at 5σ. (B) Overlay of the sAC/LRE1 complex with a sAC/ApCpp structure. Ligands and interacting residues are shown as sticks, and $Ca^{2+}$ as a sphere. (C) Overlay of sAC/LRE1 with a tmAC/forskolin complex (RMSD 9.7 Å$^2$ for 238 $C_\alpha$ atoms). The ligands are shown as sticks. (D) Overlay of sAC/LRE1 with sAC/ASI-8 (RMSD 0.3 Å$^2$ for 366 $C_\alpha$ atoms). Ligands and two key BBS residues are shown as sticks.
Figure 8:
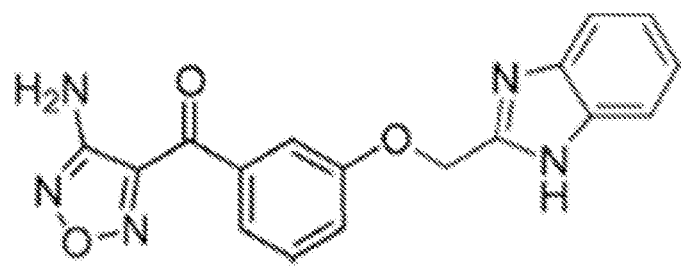
FIG. 8 shows the chemical structure of an Astex compound which is an in vitro sAC inhibitor.

To investigate how LRE1 inhibits basal sAC activity [i.e., in the absence of $HCO_3^-$ (FIG. 4D)], we compared the inhibitor complex to a sAC-cat complex with the substrate analog α,β-methylene-ATP (ApCpp; PDB code 4clk). The closest distance between inhibitor and substrate analog would be a 6.4 Å gap between the LRE1 cyclopropene and the ApCpp ribose (FIG. 7B). Thus, the inhibitor does not appear to overlap with the substrate binding site. Consistently, kinetic experiments revealed LRE1 inhibition to be non-competitive with the substrate ATP (FIG. 4F). We thus solved a sAC structure after soaking with both substrate analog ApCpp and the inhibitor LRE-1. In this structure, solved at 1.86 Å resolution (Table 1), both ligands are well defined by electron density (FIG. 4G). The inhibitor occupies an identical position as it occupies in the binary sAC/LRE-1 complex, while part of ApCpp binds differently in the trimeric complex relative to how it binds in the sAC/ApCpp complex (FIG. 4H). The adenosine moiety of the substrate analog is shifted toward the area vacated by the Arg176 reorientation, and it directly interacts with the inhibitor. Phe336 and Phe338, which are shifted due to direct interactions with the inhibitor, appear to be major factors contributing to the adenosine relocation upon LRE-1 binding. Phe336 is shifted into the original adenosine binding site which prevents regular ATP binding, and Phe338 is moved away from the active site and tears the directly interacting substrate base away from its original position. Thus, while LRE1 is not competitive with substrate binding (FIG. 4F), its presence dramatically affects ATP's position in the active site forcing it into an orientation inconsistent with catalysis.

Comparison of sAC/LRE1 with a tmAC/forskolin structure (FIG. 4C) illustrates why LRE1 is specific for sAC. The bulky tmAC activator forskolin fits into the much deeper and wider regulator binding site in tmACs, but it does not fit in the tighter sAC activation site. The position of LRE1 in sAC overlaps only with the small portion of the forskolin site in tmACs which directly corresponds to the BBS. LRE1 extends into the access channel toward the BBS, and the relatively small LRE1 is well suited for this tight channel. In contrast, LRE1 would be unable to fill most of the large activator site in tmACs, thus lacking sufficient interactions for tight binding to tmACs.

LRE1 inhibits the known physiological functions of sAC in sperm and in mitochondria.

To assess its efficacy as a physiologically relevant inhibitor, we tested whether LRE1 could inhibit known sAC-dependent functions. The first identified role of sAC was in sperm. Mammalian sperm acquire fertilization capacity as they transit through the reproductive tract in a process known as capacitation. At the molecular level, an early event in capacitation is $HCO_3^-$ induced activation of cAMP synthesis by sAC followed by the consequent activation of the main cAMP effector, Protein Kinase A (PKA). Activation of sAC and PKA precedes stimulation of a prototypical pattern of tyrosine (tyr) phosphorylation, induction of a "hyperactivated" form of motility, and finally competence to fertilize. sAC activity has been genetically and pharmacologically demonstrated to be essential for these physiological changes sperm undergo during capacitation.

Figure 5:
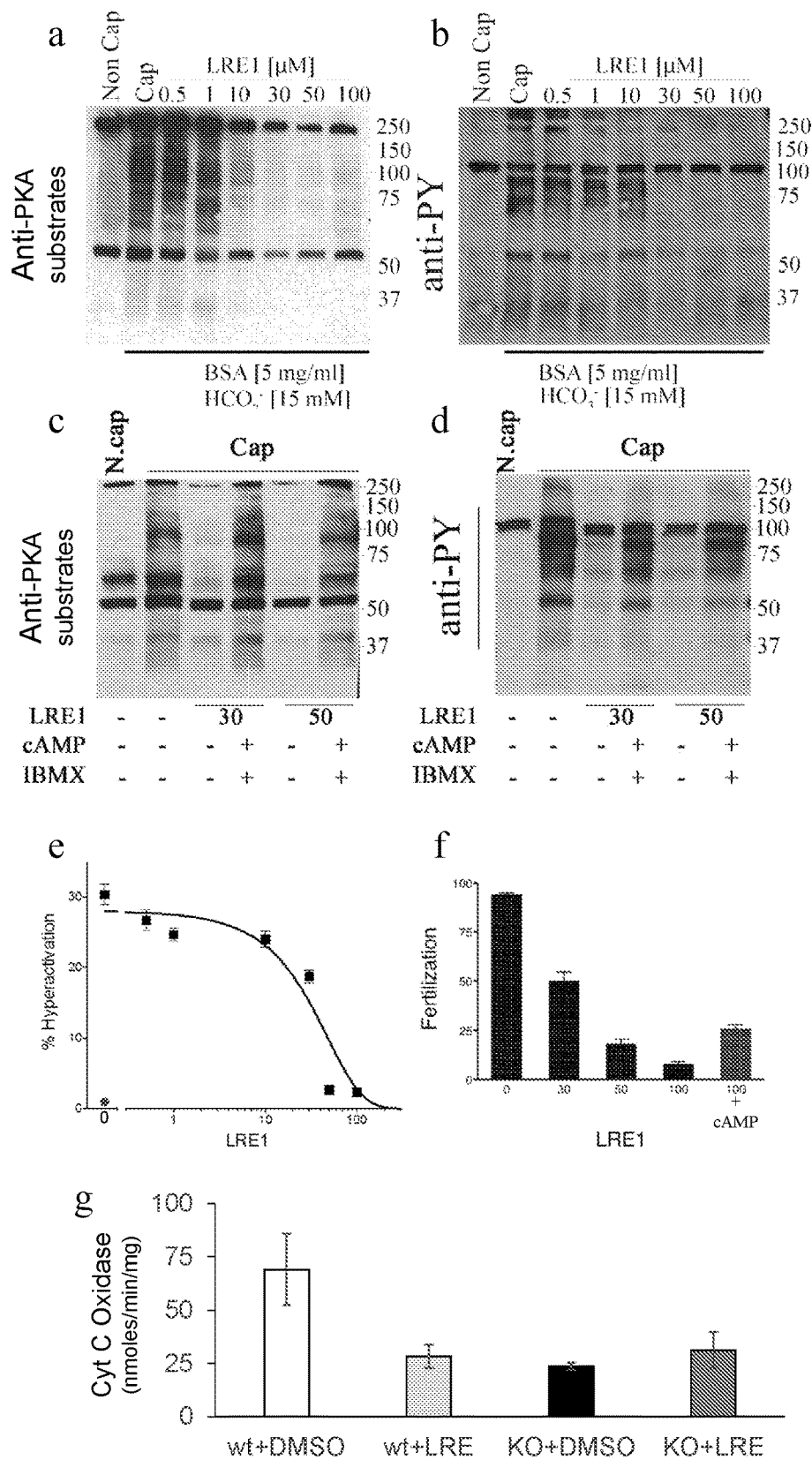
FIG. 5 shows LRE1 inhibits sAC dependent processes in sperm and mitochondria. (a-d) Sperm capacitation experiments. Mouse cauda sperm obtained in media devoid of $Ca^{2+}$, $HCO_3^-$, or BSA were activated by incubation in capacitation media containing 15 mM $HCO_3^-$, 5 mg/ml BSA, and 0.3 mM EGTA for 60 minutes in the presence of the shown amounts of LRE1. Non Cap=non capacitated negative control. Cap=DMSO treated capacitated positive control. (a) Western blot using anti-PKA substrates antibodies. (b) Western blot using anti-phospho tyrosine antibodies of the same blot as in (a). (c) Western blot using anti-PKA substrates antibodies of sperm treated with the shown amounts of LRE1 in presence (+) or absence (−) of dibutyryl cAMP (1 mM) and IBMX (100 µM). (d) Western blot using anti-phospho tyrosine antibodies of the same blot as in (c). For a-d, shown are representative Western blots of experiments repeated three times using independent sperm preparations from different mice. (e) After 60 min of incubation in capacitation media with the shown amounts of LRE1, sperm motility data were analyzed. The percentage of hyperactive sperm was assessed using parameters described for mouse sperm by the CASAnova software algorithm. Non capacitated sperm (red dot). Values are averages (±S.E.M.) of three independent sperm preparations from three different mice collected and analyzed on separate days. (f) Fertilization wells containing 25-40 eggs were inseminated with sperm that had been incubated for 1 h and 20 min in capacitation supporting Whitten's medium with the shown amounts of LRE1. Sperm in the presence of 100 µM LRE1 were also incubated in the presence of 1 mM dibutyryl cAMP (red bar). After 4 h of insemination, eggs were washed and put in fresh Whitten's media. The eggs were evaluated 24 h post-insemination. To assess fertilization, the following criteria were considered: (1) the formation of the male and female pronuclei, (2) the emission of the second polar body, and (3) two-cell stage events. Values are average percent fertilization (±S.E.M.) of four independent sperm preparations from four different mice collected and analyzed on separate days. (g) Cytochrome c oxidase (COX) activities in cells from WT and sAC KO MEFs treated with DMSO or 50 µM LRE1 for 30 min. Values are averages (±S.D.); N=5. COX activity was statistically different in WT cells±LRE1 (P=0.037) by t-test.

In sperm, LRE1 concentration-dependently blocks PKA dependent phosphorylation of its substrates (FIG. 5A, C), as well as the downstream increase in tyr phosphorylation (FIG. 5B,D), hyperactivation (FIG. 5E), and fertilization (FIG. 5F). Consistent with its effective concentration at inhibiting sAC in isolated cells (FIG. 3B,D), LRE1 inhibits these processes with an $IC_{50}$ of ~10 μM (FIG. 5). KH7 also blocked each of these sAC-dependent functions, but because the inhibitory activity of KH7 is quenched by the presence of BSA, which is an important component of capacitation-media, KH7's effect on capacitation had to be studied using other cholesterol-binding compounds (e.g., beta cyclodextrin). In contrast to KH7, LRE1 inhibition was unaffected by the presence of BSA in the incubation media (FIG. 5). Finally, confirming that LRE1 mediates its effects exclusively via inhibition of sAC, these effects of LRE1 can be rescued by addition of exogenous membrane permeable cAMP (FIG. 5C,D,F).

A second well established function of sAC is regulation of mitochondrial respiration. sAC resides in the mitochondrial matrix where it senses Krebs cycle generated $CO_2$ and hormonally stimulated calcium signals to regulate the activity of the electron transport chain. Among other potential sites of regulation, sAC generated cAMP stimulates the activity of cytochrome c oxidase (COX). LRE1 inhibits COX activity in WT MEFs, and consistent with LRE1's effects being solely mediated via inhibition of sAC, COX activity in sAC KO MEFs was unaffected by LRE1 (FIG. 5G).

LRE1 is less toxic to cells than KH7 and does not uncouple mitochondria.

Figure 6:
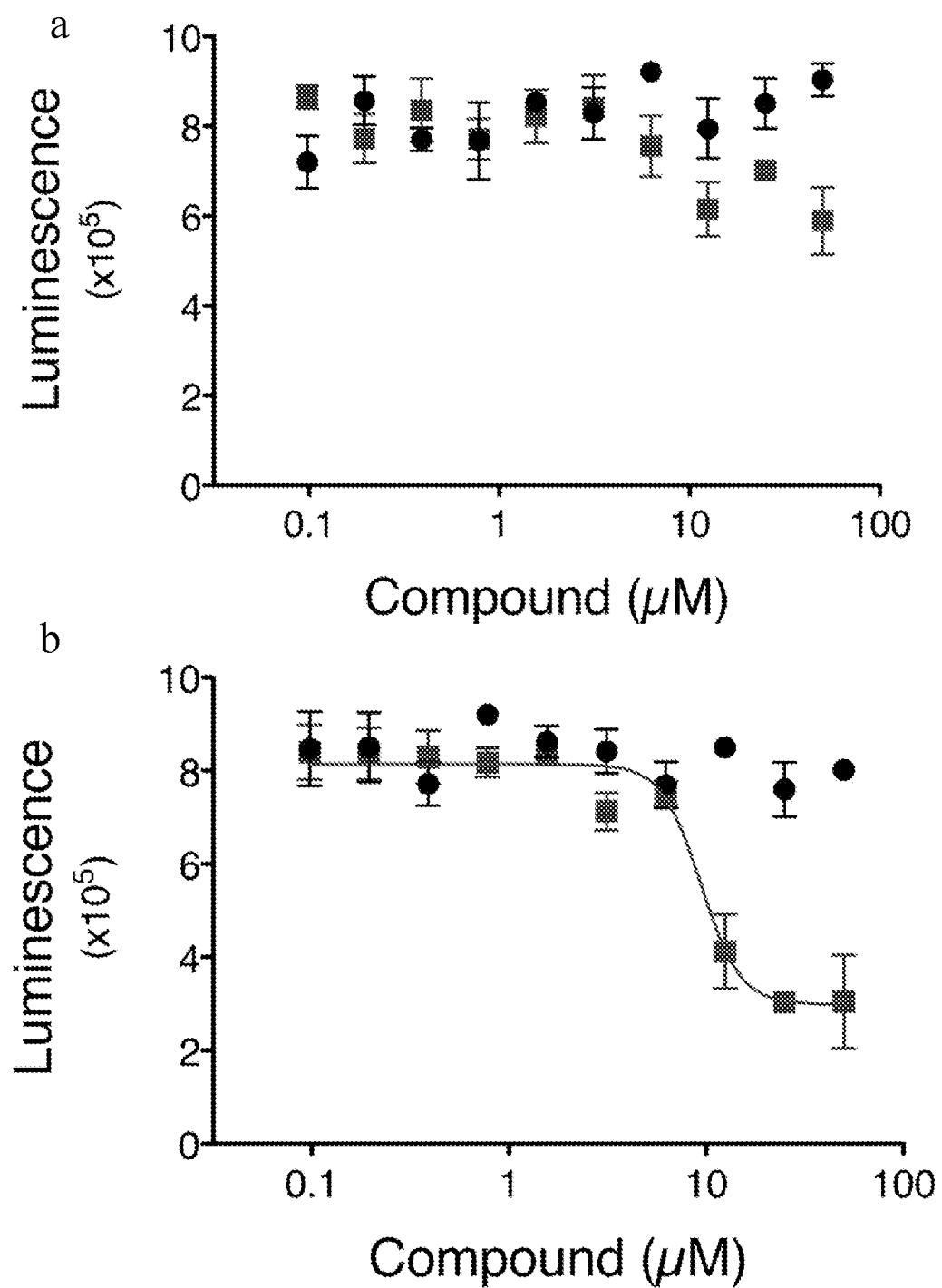
FIG. 6 shows LRE1 is less toxic than KH7. WT (a,b) or sAC KO (c) MEFs (1500 cells/well; 384 wells/plate) were grown for 24 (a) or 48 hours (b,c) in the presence of the indicated concentrations of LRE1 (circles) or KH7 (squares). Cell viability, as determined by CellTiter-Glo, is shown as luminescence; values are averages of triplicate determinations ±S.E.M. of a representative experiment repeated at least two times. (d) Changes in membrane potential (ΔΨm) in mouse brain mitochondria (at 0.2 mg/ml) incubated in 125 mM KCl, 20 mM HEPES pH 7.4, 4 mM $KH_2PO_4$, 0.5 mM EGTA, 0.2 mg/ml fatty acid free bovine serum albumin, 0.4 uM Safranin O, 5 mM pyruvate, and 2.5 mM malate in the presence of DMSO solvent alone, 50 µM LRE1, 100 µM LRE1, 50 µM KH7, or 25 µM of the classical uncoupler 2,4 dinitrophenol (2,4-DNP). Addition of Antimycin A to inhibit the mitochondrial electron transport chain confirms the mitochondrial integrity. Data represent single measurements of a representative experiment repeated at least two times.
Figure 6:
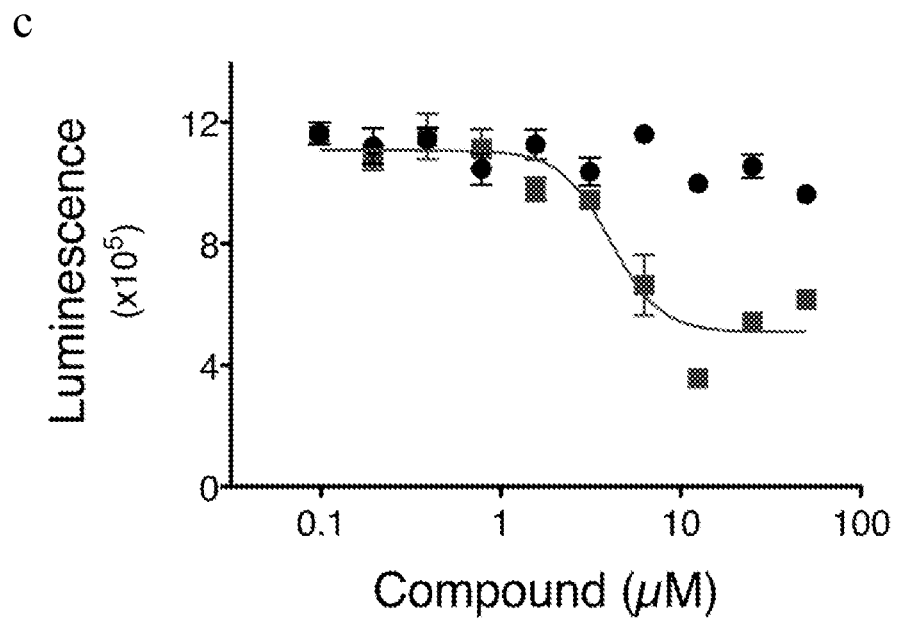
Figure 6:
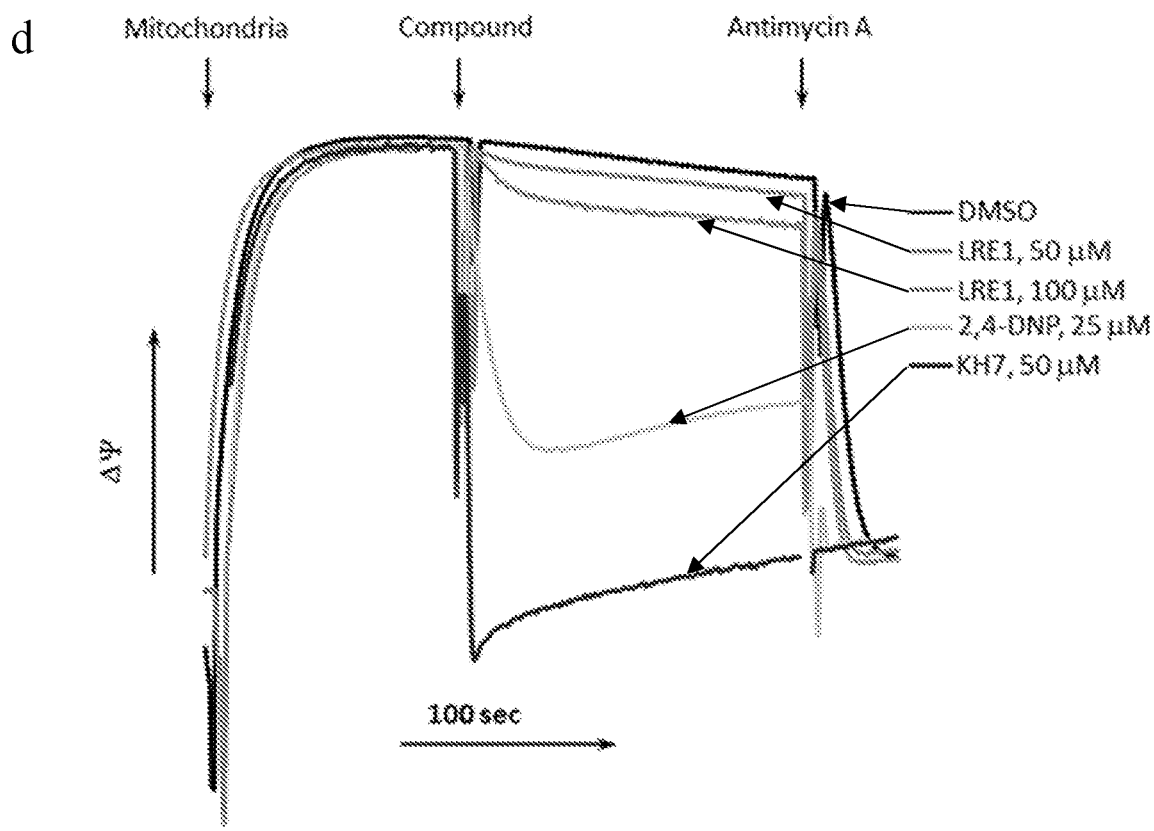

Reliable chemical probes and effective therapeutic compounds should have limited toxicity to cells with as few off-target effects as possible. Thus far, pharmacologic experiments exploring sAC function using KH7 have focused on short-term assays or single doses in vivo. In our own experience, we have observed toxicity in cells treated with KH7 for prolonged periods of time. We used two different viability assays to directly compare cellular toxicity of LRE1 and the widely used sAC specific inhibitor KH7. Using the CellTiter-Glo® high throughput viability assay (Promega Inc.), neither compound exhibited significant toxicity after a single day in culture (FIG. 6A). However, after 2 days in culture, KH7 was toxic to MEFs derived from WT C57Bl/6 mice at low μM concentrations (FIG. 6B). This toxicity was independent of sAC because KH7 exhibited a similar concentration-dependent toxicity in MEFs derived from sAC KO mice (FIG. 6C). In contrast, LRE1 was significantly less toxic than KH7; LRE1 exhibited no significant toxicity after two days in culture (FIG. 6B,C) at concentrations (i.e., up to 50 μM) which effectively inhibited sAC in cellular systems (FIG. 3B, and FIG. 5). Similar toxicity was observed using a second viability assay not dependent upon cellular ATP levels. Using the CyQUANT® cell proliferation assay (ThermoFisher), which measures viability based upon the amount of DNA in each cell, neither LRE1 nor KH7 were toxic after a single day, but on the second day, KH7, but not LRE1, was toxic at low μM concentrations. Its lack of cytotoxicity means that LRE1 does not significantly block the function of any of the 500-1500 genes required for cell survival and proliferation. These data identify LRE1 as the first pharmacological tool suitable for probing sAC functions in long-term assays.

KH7 has been reported to lead to mitochondrial uncoupling in a sAC-independent manner. At higher doses and in the absence of carrier proteins, KH7 exhibits sAC-independent, membrane perturbing effects. This off-target effect is presumably responsible for the mitochondrial uncoupling effect observed. Under conditions which reproduced KH7's uncoupling effect, LRE1 exhibited no uncoupling of isolated mouse brain mitochondria (FIG. 6D) and did not appreciably perturb bilayer properties. These studies suggest that LRE1 is a chemically inert nontoxic compound that does not interfere with essential cellular bioenergetic pathways.

Figure 9:
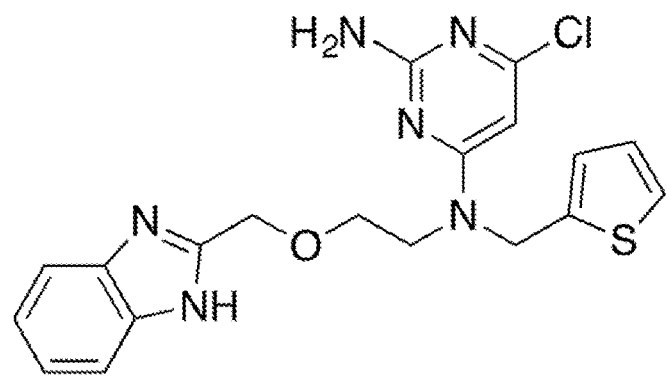
FIG. 9 shows the chemical structure of TDI-006145-NX-1, which is potentially equivalent to LRE1.
Figure 10:
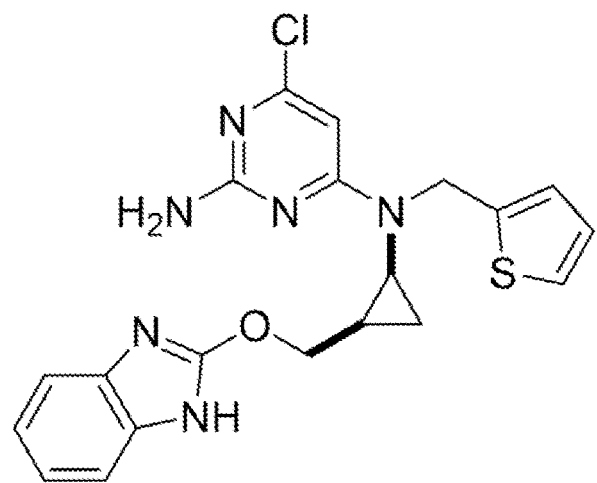
FIG. 10 shows the chemical structure for TDI-006281-NX-1, which is potentially equivalent to LRE1.
Figure 11:
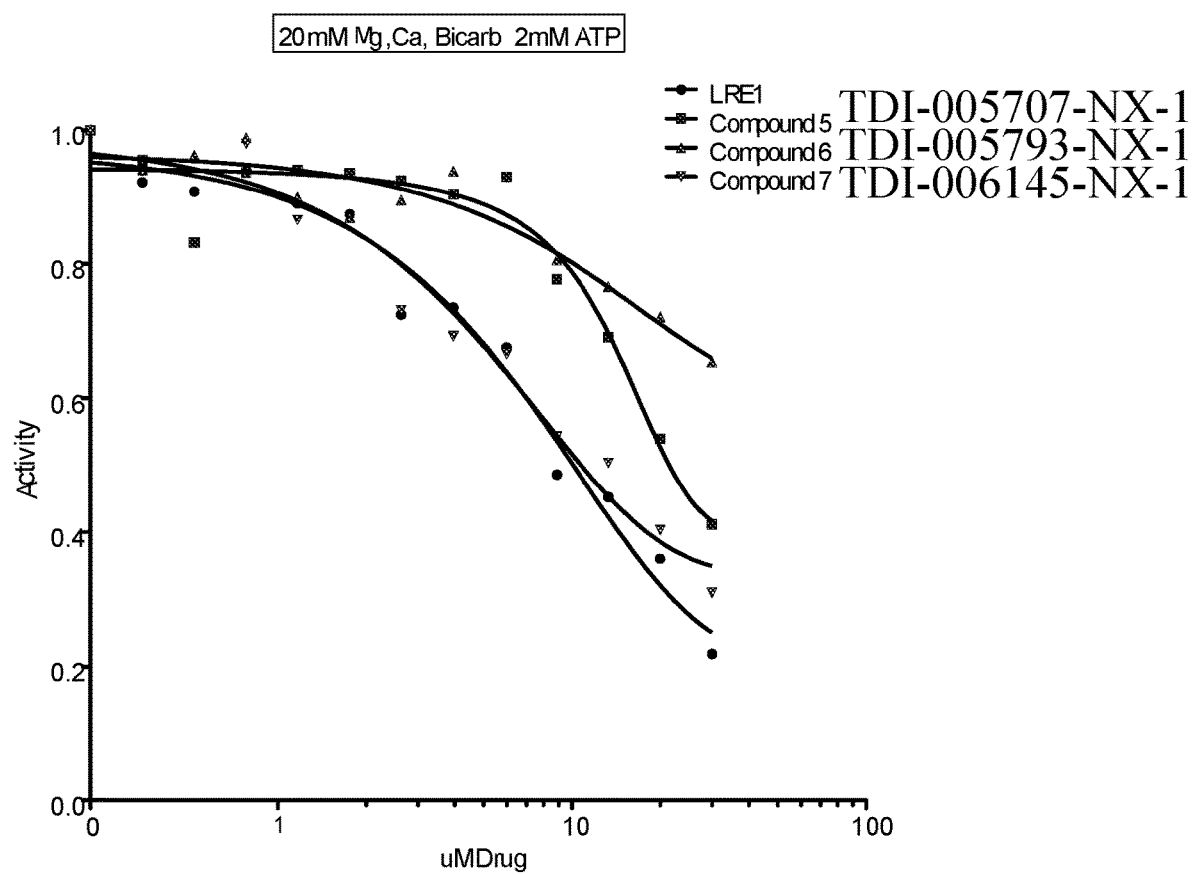
FIG. 11 shows a Concentration-response curve of LRE1 (circles), plus compounds TDI-005707-NX-1 (squares), TDI-005793-NX-1 (triangles, ▲), TDI-006145-NX-1 (inverted triangles, ▼) on sAC protein in the presence of 2 mM ATP/10 mM $MgCl_2$/10 mM $CaCl_2$/40 mM $NaHCO_3$. Values are pmol units of cAMP formed per minute in the presence of the indicated concentrations of each compound; shown is a representative experiment repeated at least two times.
Figure 12:
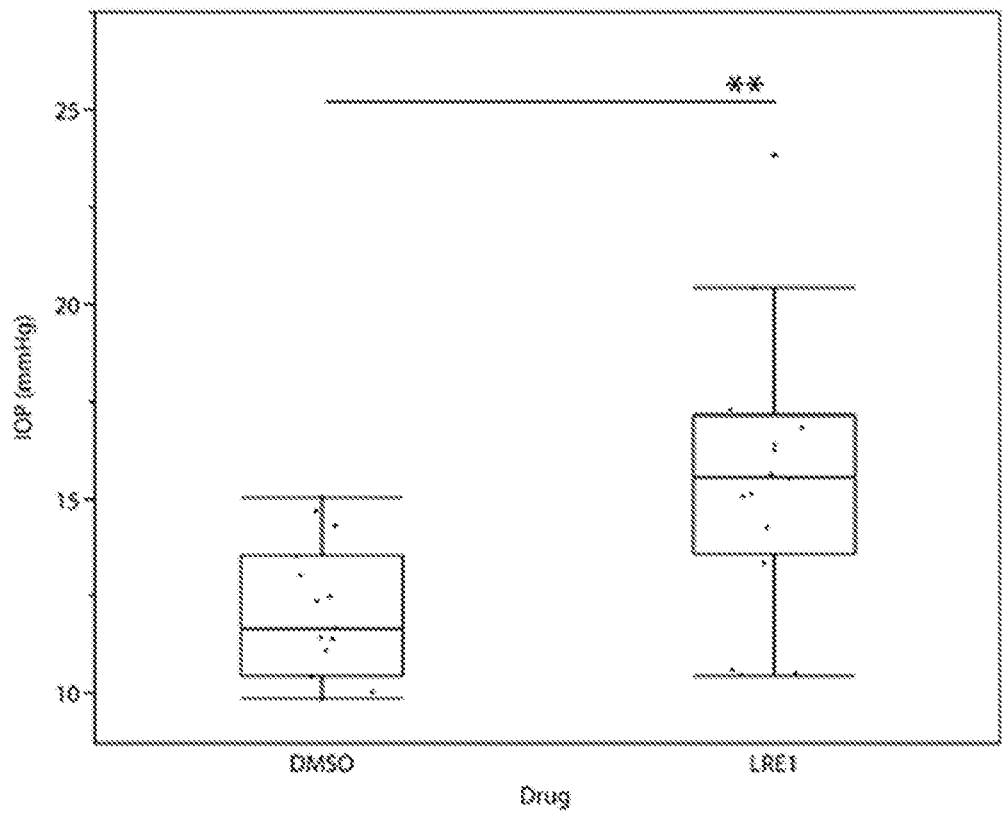
FIG. 12 shows intraocular pressure (IOP) in avertin-anesthetized mice. Graphs of IOP measurements in avertin-anesthetized mice by direct cannulation (n=8). ** indicates p<0.01. C57BL/6J mice were administered DMSO solubilized sAC inhibitor (LRE-1) by intraperitoneal injection. Two hours post-treatment, mice were anesthetized with avertin, and IOP was measured by direct cannulation of the anterior chamber.
Figure 13:
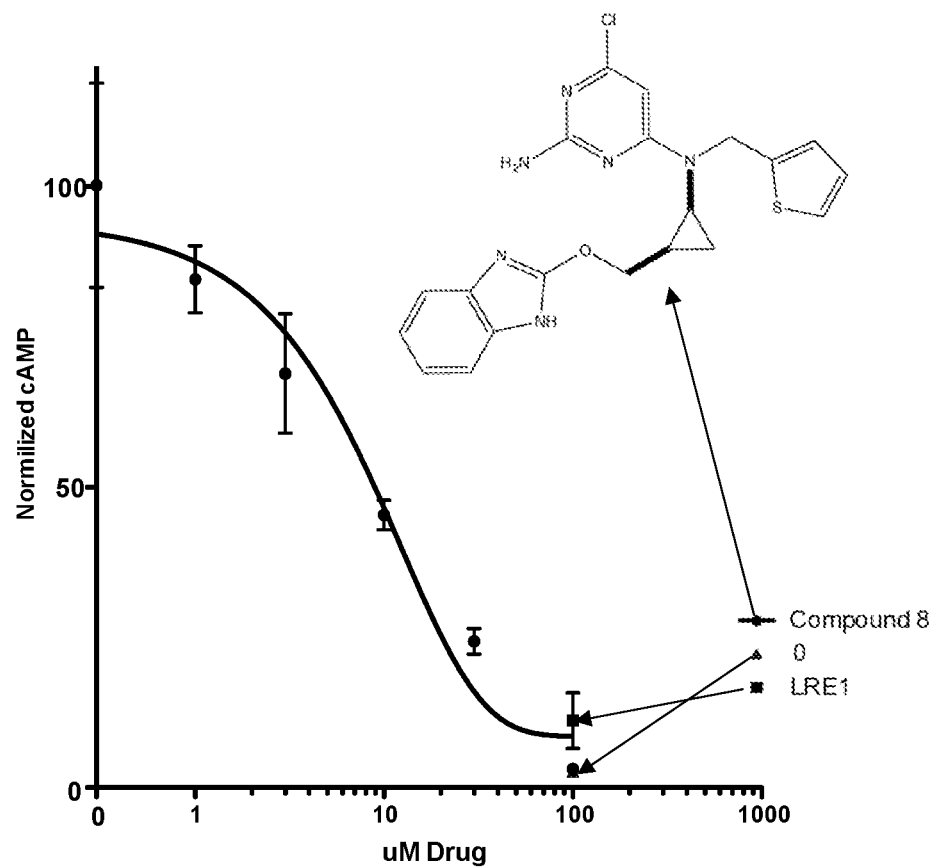
FIG. 13 shows LRE1 and NCEs inhibit sAC activity inside cells. Concentration-response of (A) TDI-006281-NX-1 (circles), (B) TDI-006145-NX-1 (circles), or (C) LRE1 (squares) and KH7 (circles) on cellular accumulation of cAMP measured in the presence of the phosphodiesterase (PDE) inhibitor (0.5 mM) IBMX, in sAC overexpressing 4-4 cells. In sAC overexpressing 4-4 cells, in the presence of PDE inhibitors, the cAMP accumulation inside cells is almost exclusively due to cellular sAC activity. The two NCEs have approximately the same concentration dependency as the parent compound, LRE1 (panel C=curve reprinted from Ramos-Espiritu et al: concentration-dependent response of 1 rel and KH7 on cellular accumulation of cAMP in sAC-overexpressing 4-4 cells.
Figure 13:
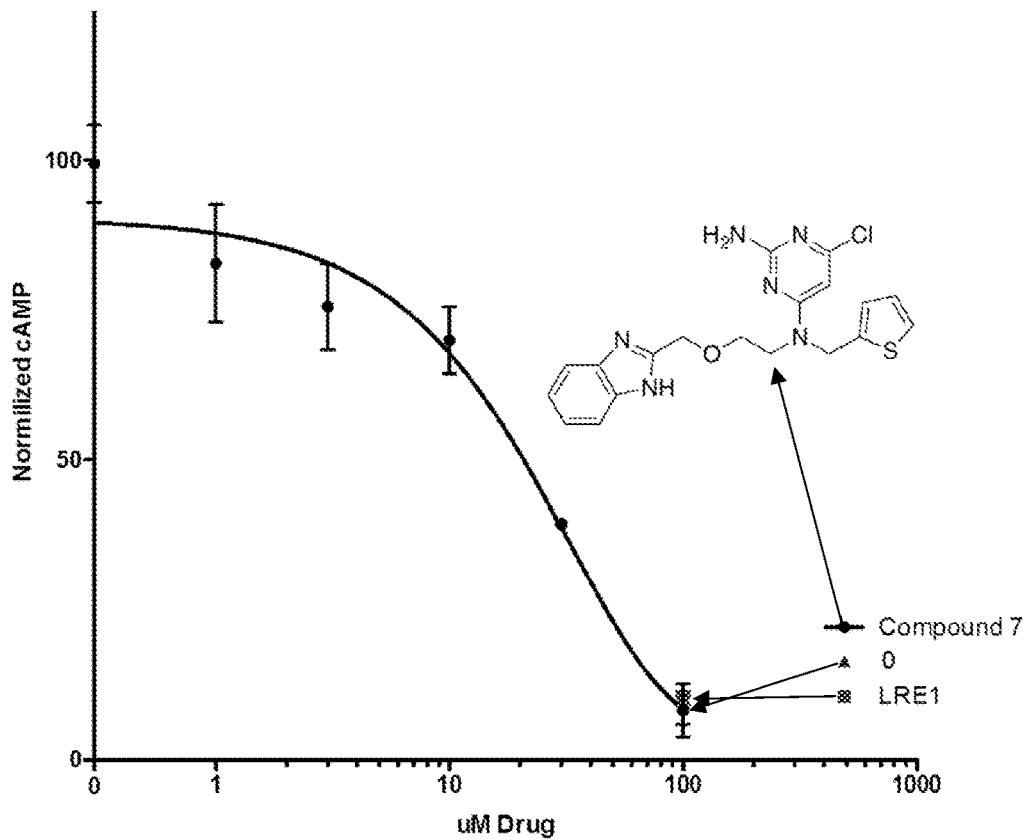
Figure 13:
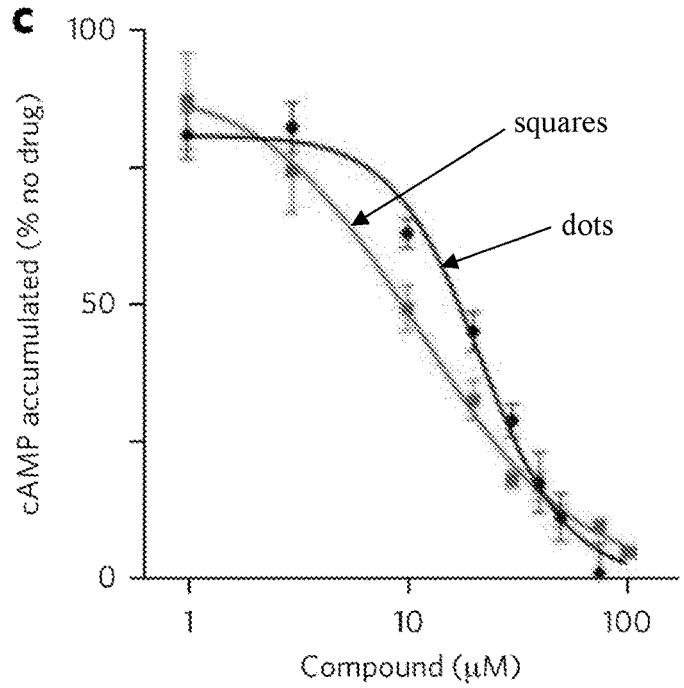
Figure 14:
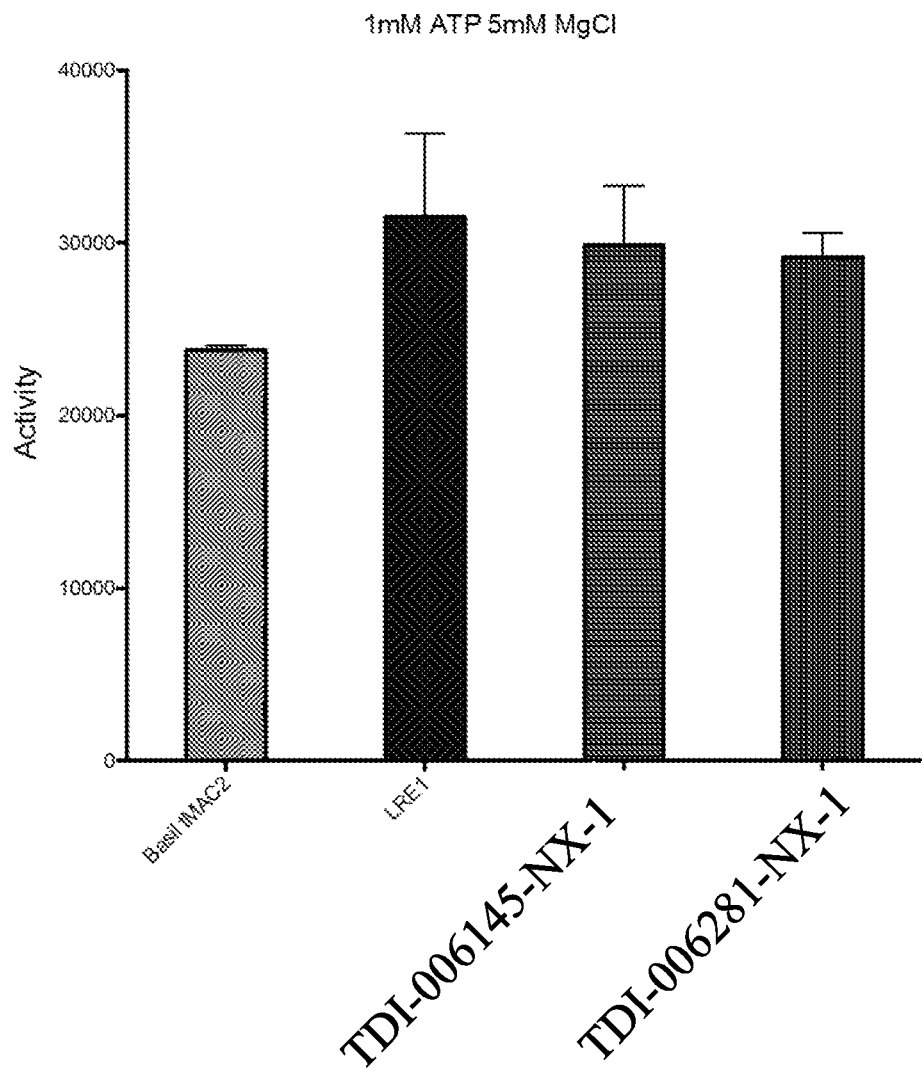
FIG. 14 shows an in vitro assay of tmAC type 2. LRE1 related NCEs also have small stimulatory effect on tmAC2. In vitro adenylyl cyclase assay in extracts from tmAC type 2 transfected cells. Shown is basal cyclase assay in the absence (left bar) or presence of 30 µM LRE1 (second from left bar), or 30 µM LRE1-7 (TDI-006145) (third from left bar) or 30 µM LRE1-8 (TDI-006281) (right bar).

Some exemplary compounds of the present disclosure are shown in FIGS. 9 (TDI-006145-NX-1) and 10 (TDI-006281-NX-1). The activity of TDI-006145-NX-1 and TDI-006281-NX-1 relative to LRE1 is shown in FIG. 11. Experiments were conducted to evaluate the effects of LRE1 on intraocular pressure (TOP) in mice. Results are shown in FIG. 12 indicating LRE1 is able to increase the IOP. Both TDI-006145-NX-1 and TDI-006281-NX-1 have similar concentration dependency as LRE1 (FIG. 13). Further, LRE1, and both TDI-006145-NX-1 and TDI-006281-NX-1 exhibited a small stimulatory effect on tmAC in an in vitro assay (FIG. 14).

The RF-MSS cyclase assay we have developed, based upon MS determination of both cAMP produced and ATP consumed, combines the specificity and broad dynamic range of a radioactive substrate assay with the high throughput adaptability of more modern methods. By measuring both product formation and substrate consumption, the RF-MSS assay substantiates that product is derived from input substrate. The sensitivity and dynamic range of the assay will depend upon the particular Mass Spectrometer used; in our case the Agilent 6520 TOF MS has a theoretical limit of high femtogram sensitivity and up to 5 orders of magnitude dynamic range. Finally, using the RapidFire delivery system, we experienced cycle times of 15 seconds per sample, which not only supplied high throughput capability, but also facilitated kinetic analysis. In addition, the RF-MSS is non-radioactive which provides for a safer assay with less environmental impact, and it is not dependent upon consumable and often non-renewable reagents such as antisera. Thus, the RF-MSS assay has the potential to effectively replace previously existing adenylyl cyclase assays.

Using the RF-MSS assay, we identified a new sAC-specific inhibitor, LRE1. Among the different adenylyl cyclase inhibitors known, those structurally studied and mechanistically understood target the substrate binding region (e.g., P site inhibitors) or its immediate environment (e.g., catechol estrogens, DIDS). Crystallographic and kinetic data reveal that LRE1 specifically inhibits sAC via a novel allosteric mechanism induced through binding to its unique bicarbonate binding site (BBS). The corresponding site in tmACs is where the tmAC-specific activator forskolin binds. Forskolin is considerably larger than bicarbonate (FIG. 7C), and it does not fit in sAC's BBS. This difference in size between the forskolin binding site of tmACs and the BBS of sAC allows highly specific ligand interactions explaining the selective inhibition of sAC by LRE1. LRE1 not only occupies the BBS, it also extends into the channel connecting the BBS to the active site which provides additional favorable interactions for specific and tight ligand binding. This channel is also the binding site of the structure-based designed inhibitor, ASI-8 (FIG. 7D), and it is postulated to be the site of KH7 inhibition of sAC. However, both KH7 and ASI-8 are long compounds which would extend into the active site and inhibit, at least partially, via competition with the substrate. Consistently, LRE1 is non-competitive with ATP (FIG. 4F); thus, LRE1 is the only known, exclusively allosteric inhibitor of sAC. Despite this shorter cyclopropane extension (as compared to ASI-8 and KH7), LRE1 still exhibits high affinity. Presumably, its affinity is augmented by additional interactions from the branching thiophene moiety, which exploits an additional sAC pocket (FIG. 7D). These data identify LRE1 as the first potent and selective pharmacological modulator which acts allosterically via BBS binding. Thus, our study reveals that drug-like ligands can bind tightly to the BBS and allosterically inhibit sAC, and it raises the possibility that pharmacological ligands could mimic the stimulating effect of the small physiological sAC activator bicarbonate.

LRE1 combines high potency and selectivity with stability, solubility and, most importantly, lack of cytotoxicity. In particular, LRE1 exhibits less non-specific toxicity than KH7, the widely used sAC specific inhibitor, and bithionol, a recently characterized sAC selective inhibitor. Therefore, LRE1 is an ideal candidate to explore the therapeutic possibilities of sAC inhibition.

In summary, we have exploited the RapidFire mass spectrometry system (RF-MSS) to develop a safe and robust adenylyl cyclase assay suitable for a wide variety of applications. Using this RF-MSS cyclase assay, we identified an improved sAC specific inhibitor, LRE1, which occupies the regulatory "activator" site to allosterically inhibit the enzyme, and which exhibits pharmacologically favorable characteristics.

Databases

Crystal structures and diffraction data have been deposited with the worldwide protein data bank (wwPDB) under accession codes 5IV4 (sAC/LRE1) and 5IV3 (sAC/LRE1/ApCpp).

Methods

Chemicals and Cell Lines

All chemicals were purchased from Sigma Aldrich (St. Louis, Mo.) unless otherwise noted. KH7 and LRE1 were synthesized by The Milstein Synthetic Chemistry Core Facility at Weill Cornell Medical College. Small molecules were purchase as powder and suspended in DMSO. Anti-phosphotyrosine (anti-PY) monoclonal antibody (clone 4G10) was obtained from Millipore (Billerica, Mass.), and rabbit monoclonal anti-phosphoPKA substrates (clone 100G7E) was purchased from Cell Signaling (Danvers, Mass.).

4-4 cells, sAC KO MEFs, and WT MEFs were generated and functionally authenticated in our laboratory as previously described[41] and grown in DMEM+10% FBS. INS-IE cells were obtained directly from P. Antinozzi and C. Wollheim and functionally authenticated in our laboratory. They were cultured in RPMI media containing 10% heat-inactivated FBS, 10 mM HEPES, and 1 mM sodium pyruvate, 50 μM β-mercaptoethanol, and passaged every 2-3 days. All cells were maintained at 37° C. in 5% $CO_2$ and are periodically checked for mycoplasma contamination.

RapidFire Mass Spectroscopy

Analyses of cyclase assays were performed on an Agilent Rapid Fire 365 high throughput Mass Spectroscopy System (RF-MSS), equipped with an Agilent 6520 TOF accurate mass spectrometer as a detection system (Agilent Technologies, Woburn, Mass.). This instrument also includes a Zymark Twister® robotic arm that handles microtiter plates and a purification SPE system. 35 μl of sample was aspirated from each well of a 384-well reaction microtiter plate and then injected onto a graphitized carbon SPE column extraction cartridge, washing with aqueous alkaline buffer and eluting it in an alkaline/organic solvent, onto the electrospray-MS, where the mass spectra of each sample was collected. The RapidFire sipper was washed between sample injections using organic (25% acetonitrile, 25% acetone in 5 mM ammonium acetate, pH 10) and aqueous (5 mM ammonium acetate, pH 10) solvents. RapidFire mass spectrometry screening data were processed and analyzed using Agilent MassHunter Software.

For in vitro cyclase assays, human $sAC_t$ protein was assayed in the presence of 50 mM Tris pH 7.5, 2 mM DTT, 5 mM $MgCl_2$, and the indicated concentration of ATP in the presence or absence of 5 mM $CaCl_2$ and/or 40 mM $NaHCO_3$. cAMP produced and ATP consumed were determined by RF-MSS in comparison with standards of known concentrations, and for all quantitative cAMP measurements, we confirmed there was a corresponding decrease in input ATP. Mammalian tmAC isozymes tmAC I (ADCY1; bovine), tmAC II (ADCY2; rat), tmAC V (ADCY5; rat), tmAC VIII (ADCY8; rat), and tmAC IX (ADCY9; mouse) were transfected and expressed in HEK293 cells using the CMV promoter and whole cell extracts were assayed in the presence of 100 μM GTPγS via the classical two column radioassay measuring conversion of [$^{32}$P] ATP into [$^{32}$P] cAMP as described previously[86].

Small Molecule Library 33,135 compounds were selected from a larger set of 7.87 million commercially available screening compounds. The strategy for purchasing these compounds was to maximize coverage of chemical space and "drug-likeness" properties based on quantitative scores, while simultaneously minimizing cost. Pipeline Pilot software (Dassault Systemes Biovia Corp., San Diego, Calif.) was used to execute a published algorithm for scoring compounds based on drug-likeness, called the quantitative exponent of drug-likeness (Q.E.D.) score. From the 7.87 million commercially available compounds, 3.05 million compounds had a weighted Q.E.D. score greater than 0.7. The "choose diverse" component of the Pipeline Pilot software utilizes ECFP6 fingerprint descriptors to cluster the compounds into structurally related groups and chooses a single representative of each cluster, based on Tanimoto distances, called "cluster centers". The "choose diverse" component identified 100,000 relatively diverse compounds from among these 3.05 million structures. From these 100,000 "cluster centers," 33,135 could be purchased from Enamine Ltd. (Princeton, N.J.) in 1 mg quantities at a price which was within our budgetary limits. These compounds were formatted in 10 copies of 5 mM DMSO stocks in 384-well deep well plates for screening.

High-Throughput Screening

The primary screen was performed in polystyrene 384-well microplates (Greiner Bio One International AG). 33,135 compounds were screened at 10 μM. The reagents were dispensed using a liquid handling instrument Multi-drop™ Combi Assay buffer (50 mM Tris pH 7.5, 5 mM $CaCl_2$, 5 mM $MgCl_2$, 40 mM $NaHCO_3$, 2 mM DTT) was added first on the 384-well plate (Greiner Bio-One) followed by the compounds. The small molecule compounds were dispensed with a nanohead containing a 384-well array of Norgren Kloehn nanosyringes, and each plate was barcoded. The human $sAC_t$ protein was added next followed by the remainder of the assay buffer. The stop reaction buffer (1% formic acid) was added to the last column of each plate (denatured protein; T0). Reactions were started by addition of ATP at a final concentration of 1 mM. Reactions were incubated for 3 hours at 37° C., and stopped with the addition of 1% formic acid.

Cellular cAMP Accumulation Assays sAC KO MEFs or 4-4 cells (2.0×10$^6$ cells/ml) in suspension were transferred in 1.5 ml tubes and incubated at 37° C., 5% $CO_2$ for one hour. A time zero value for each condition was determined by adding 100 μl of cells directly into 100 μl stop solution (0.2 M HCl). To measure cAMP accumulation, cells in suspension were incubated for the indicated period of time in the presence of 500 μM IBMX (+/−LRE1 or +/−KH7) at 37° C. after which 100 μl of cells were transferred to a fresh tube containing stop solution. Intracellular cAMP content was determined using Correlate-EIA™ Direct Assay (Assay Designs, Inc). INS-1E insulinoma cells were incubated in 2.5 mM glucose Krebs-Ringer buffer (pH 7.5) supplemented with 2 mM sodium bicarbonate, 10 mM HEPES, and 0.1% BSA for 2 h before start of the experiment. At time zero for each experiment, media was switched to Krebs-Ringer buffer containing 2.5 mM glucose or 16 mM glucose in the presence of 500 μM IBMX and inhibitor at the shown concentrations. After 10 min cells were lysed in 200 μl 0.1 M HCl. Intracellular cAMP contents were determined using Correlate-EIA™ Direct Assay (Assay Designs, Inc).

Crystal Structure Determination of sAC Complexes

Protein for crystallization comprised the catalytic domains of human sAC (residues 1-469; sAC-cat), corresponding to the native $sAC_t$ isoform, and a C-terminal his-tag. sAC-cat was expressed in Hi5 insect cells using the BIIC-method and purified by nickel affinity chromatography, anion exchange and size exclusion chromatography as described previously (Kleinboelting et al., Acta Crystallogr. F, 70, 467-469 (2014)). Apo sAC-cat was crystallized using the hanging drop method at 4° C. as described (Kleinboelting et al., Acta Crystallogr. F, 70, 467-469 (2014)). Crystals were soaked with LRE-1 by transferring them into cryo solution (100 mM sodium acetate pH 4.8, 200 mM trisodium citrate, 18% (w/v) PEG 4000, 20% (v/v) glycerol) supplemented with 20 mM LRE1 alone or together with 150 mM ApCpp, 75 mM $MgCl_2$/$CaCl_2$ and incubation for 24 h at 4° C. Crystals were flash-frozen in liquid nitrogen, and a complete dataset (space group $P6_3$) was collected from one crystal at 100 K at the Berlin Electron Storage Ring society for Synchrotron Radiation beamline 14.1 (BESSY BL14.1) operated by Helmholtz-Zentrum Berlin. All diffraction data were processed with XDSAPP, with the resolution limit set automatically using CC*. Molecular replacement phasing with the apo sAC structure (pdb code 4cll) as a search model, manual model building and refinement were done as described for previous sAC/ligand complexes (Kleinboelting et al., Proc. Natl. Acad. Sci. U.S.A., 111, 3727-3732 (2014)). Structure figures were generated with PyMol (www.pymol.org).

Cheminformatics and Data Handling

Data from all screening studies are archived and analyzed using the CDD Vault from Collaborative Drug Discovery (Burlingame, Calif. www.collaborativedrug.com). MarvinSketch (ChemAxon, Budapest, version 14.9.8.0) was used for drawing and naming chemical structures. Instant Jchem for Excel (ChemAxon, Budapest Hungary, version 15.8.24.0) was also used for creating structure spreadsheets and tables. Compound similarity search was performed using Pipeline Pilot version 9.2 (Dassault Systemes Biovia Corp., San Diego, Calif.). Graphpad PRISM (www.graphpad.com, version 6.05) was used for curve fitting.

Sperm Assays

Mouse sperm were isolated as described (Navarrete et al., J. Cell Physiol., 230, 1758-1769 (2015)). Sperm were incubated in Toyoda-Yokoyama-Hosi (standard TYH) medium buffered with 25 mM bicarbonate in 5% $CO_2$ for sperm capacitation and fertilization assays. Western blot and motility assays were performed in Hepes-buffered TYH (H-TYH). For capacitation, 15 mM $NaHCO_3$ and 5 mg/ml BSA was added, and sperm incubated at 37° C. for at least 1 hour. For LRE1 treatment, sperm were pretreated for 10 min with LRE1 before addition of capacitation medium and/or dibutyryl cAMP. Anti-PKA substrates and anti-pY western blots, in vitro fertilization (IVF), and sperm motility analysis using a CEROS computer-assisted semen analysis (CASA) system (Hamilton Thorne Research, Beverly, Mass.) were performed as described (Navarrete et al., J. Cell Physiol., 230, 1758-1769 (2015)). At least 20 microscopy fields corresponding to a minimum of 200 sperm were analyzed in each motility experiment.

Mitochondrial COX Activity

Wild type and sAC KO MEFs were plated in P10 dishes. At 70% of confluence cells were incubated at 37° C. with DMSO or LRE1 50 μM for 30 min in serum free medium. Subsequently the cells were scraped in PBS and centrifuged for 5 min at 1000 rpm. The pellet was snap frozen in liquid nitrogen and stored at −80° C. Before the experiment the pellets were resuspended in PBS, COX activity was measured as described previously (Birch-Machin et al., Method Cell Biol., 65, 97-117 (2001)) and normalized to protein concentration.

Cytotoxicity Assays

Cells were plated in 384- or 96-well plates. The next day, compounds were added (ten concentrations), and the plates were incubated for 24 or 48 hrs at 37° C./5% $CO_2$, and viability was quantified by measuring cellular ATP using luminescence (CellTiter-Glo®, Promega, Madison, Wis., USA) or viability based upon amount of DNA (CyQUANT®, ThermoFisher).

Measurement of the Membrane Potential in Isolated Mouse Brain Mitochondria

Mouse brain mitochondria were isolated by the Percoll gradient method as described (Sims et al., J. Neurochem., 55, 698-707 (1990)) and re-suspended in 90 μl of isolation medium containing 225 mM mannitol, 75 mM sucrose, 20 mM HEPES-KOH (pH 7.4), 1 mM EGTA, and 0.2 mg/ml fatty acid-free bovine serum albumin (BSA). The membrane potential changes were assessed from the changes in fluorescence of a permeating cation Safranin O at 495 nm excitation and 586 nm emission wavelength with Hitachi F-7000 spectrofluorimeter (Hitachi, Japan). The incubation medium was composed of 125 mM KCl, 20 mM HEPES (pH 7.4), 4 mM KH2PO4, 0.5 mM EGTA, 0.2 mg/ml BSA, 2 μM Safranin O (membrane potential probe), 5 mM Pyruvate, 2.5 mM malate, and 0.1 mg/ml mitochondria protein.

General Synthetic Scheme of TDIW-167-01

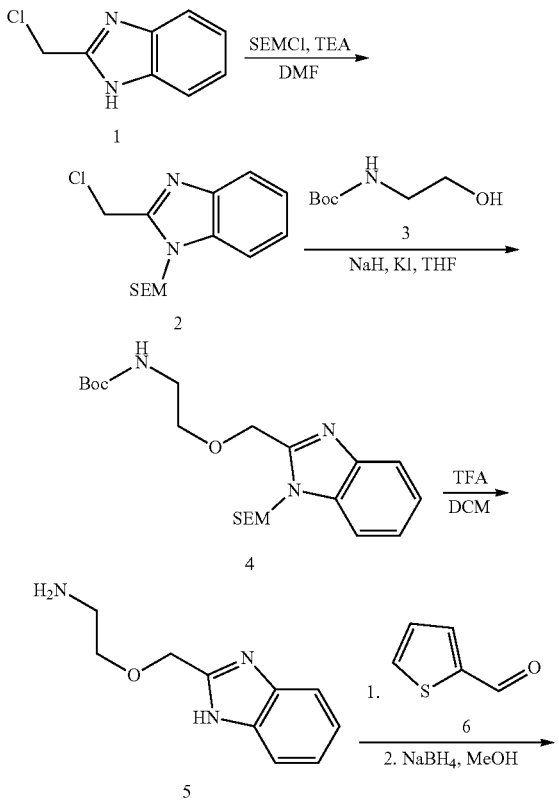

27
-continued
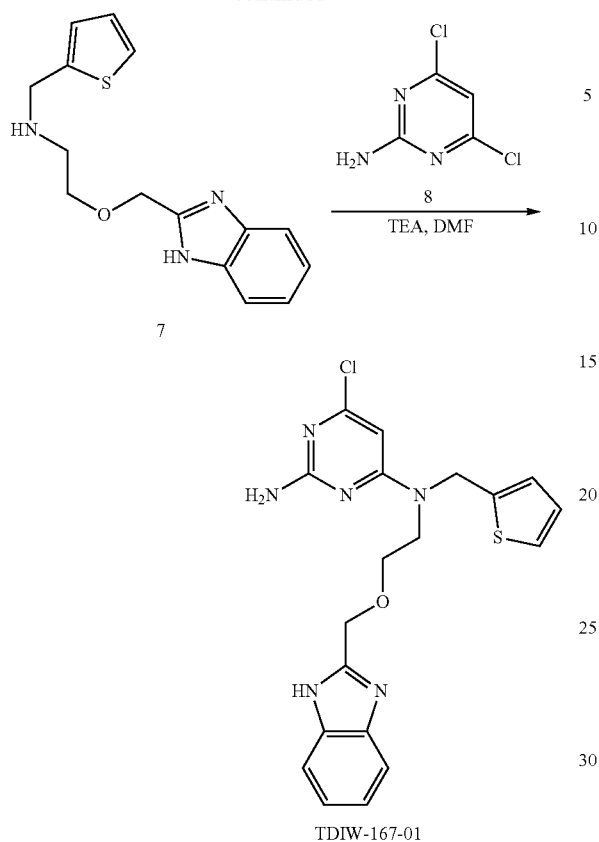
TDIW-167-01
General Synthetic Scheme of TDIW-167-02
28
-continued
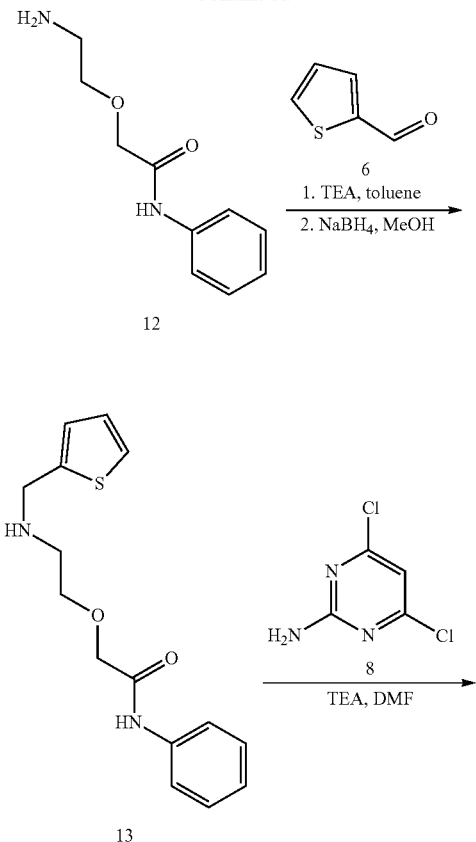
13
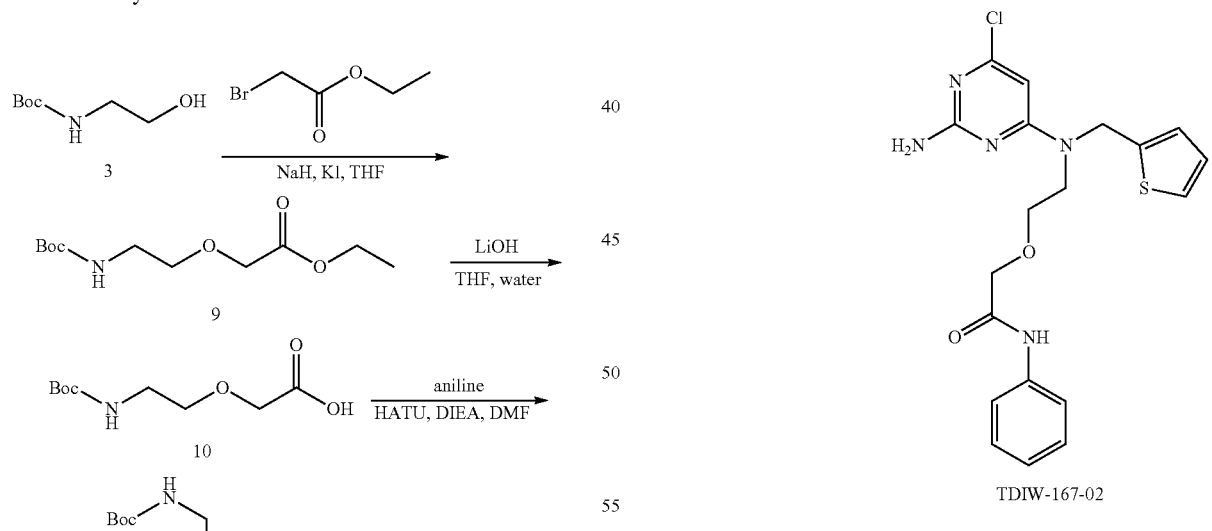
TDIW-167-02
General Synthetic Scheme of TDIW-167-03
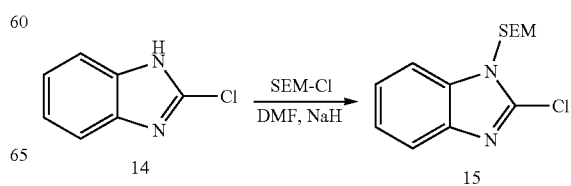

Synthetic Procedures
Preparation of Compound 2

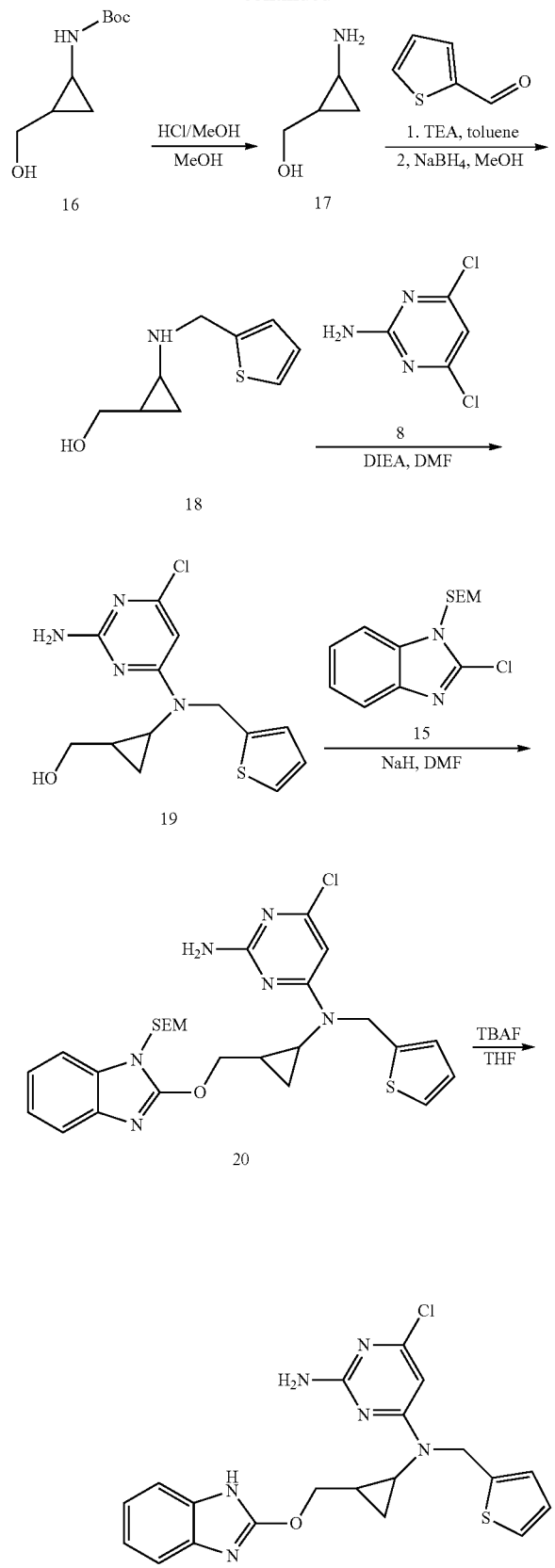

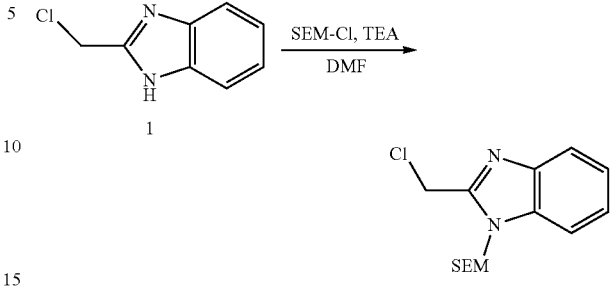

To a solution of compound 1 (3.33 g, 19.99 mmol, 1.00 eq) in N, N-dimethylformamide (33 mL) was added triethylamine (6.07 g, 59.97 mmol, 8.32 mL, 3.00 eq). After 10 min, 2-(trimethylsilyl)ethoxymethyl chloride (6.66 g, 39.98 mmol, 7.09 mL, 2.00 eq) was added at 0° C. The mixture was stirred at 25° C. for 15 hours under nitrogen atmosphere. TLC (petroleum ether:ethyl acetate=5:1) showed the starting material was consumed and a new spot was detected. The mixture was quenched with water (50 mL) and then extracted with ethyl acetate (40 mL*3). The combined organic layer was washed with brine (30 mL*3), dried over anhydrous sodium sulfate, filtered, and concentrated in vacuo to give compound 2 (1.2 g, 2.82 mmol, 14.12% yield, 69.82% purity) as yellow oil.

LCMS: RT=0.856 min, m/z 297.1 [M+H]$^+$, purity=69.82%

$^1$H NMR (CDCl$_3$, 400 MHz) δ 7.78 (d, J=7.2 Hz, 1H), 7.49 (dd, J$_1$=1.2, J$_2$=7.2 Hz, 1H), 7.36-7.30 (m, 2H), 5.65 (s, 2H), 4.91 (s, 2H), 3.57 (t, J=8.0 Hz, 2H), 0.92 (t, J=8.4 Hz, 2H), −0.04 (s, 9H).

Preparation of Compound 4

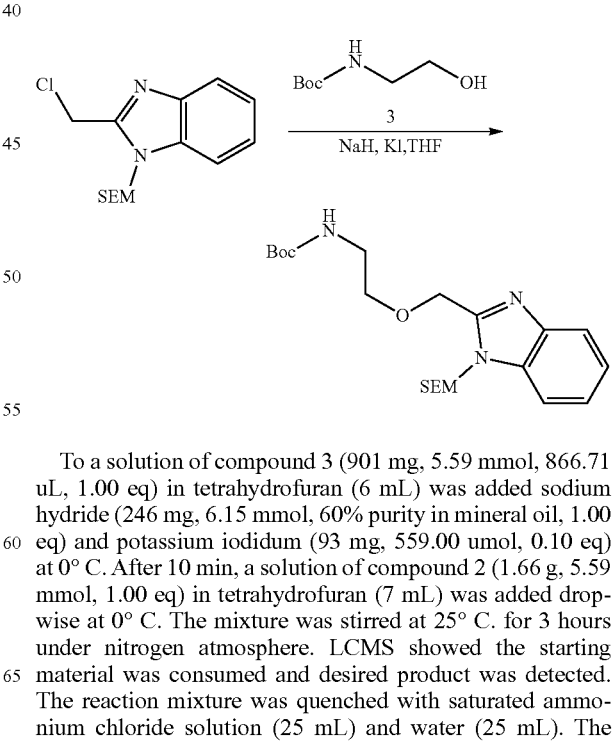

To a solution of compound 3 (901 mg, 5.59 mmol, 866.71 uL, 1.00 eq) in tetrahydrofuran (6 mL) was added sodium hydride (246 mg, 6.15 mmol, 60% purity in mineral oil, 1.00 eq) and potassium iodidum (93 mg, 559.00 umol, 0.10 eq) at 0° C. After 10 min, a solution of compound 2 (1.66 g, 5.59 mmol, 1.00 eq) in tetrahydrofuran (7 mL) was added dropwise at 0° C. The mixture was stirred at 25° C. for 3 hours under nitrogen atmosphere. LCMS showed the starting material was consumed and desired product was detected. The reaction mixture was quenched with saturated ammonium chloride solution (25 mL) and water (25 mL). The mixture was extracted with ethyl acetate (50 mL*3). The combined organic layers were washed with brine (30 mL*2), dried over anhydrous sodium sulfate, filtered and concentrated in vacuo to give compound 4 (2.58 g, crude) as yellow oil.

LCMS: RT=0.855 min, m/z 422.2 [M+H]$^+$, purity=57.43%

$^1$H NMR (CDCl$_3$, 400 MHz) δ 7.77 (dd, J$_1$=7.2 Hz, J$_2$=2.0 Hz, 1H), 7.49 (dd, J$_1$=6.8 Hz, J$_2$=1.2 Hz, 1H), 7.36-7.30 (m, 2H), 5.62 (s, 2H), 5.21 (br. s, 1H), 4.87 (s, 2H), 3.72 (t, J=4.8 Hz, 2H), 3.57 (t, J=8.0 Hz, 2H), 3.32-3.28 (m, 2H), 1.43 (s, 9H), 0.92 (t, J=8.4 Hz, 2H), −0.04 (s, 9H).

Preparation of Compound 5

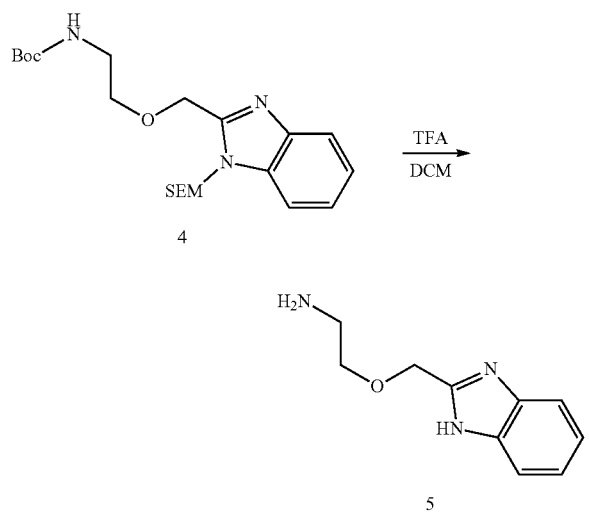

To a solution of compound 4 (2.58 g, 6.12 mmol, 1.00 eq) in dichloromethane (5 mL) was added trifluoroacetic acid (30.8 g, 270.14 mmol, 20 mL, 44.14 eq) drop wise at 0° C. The mixture was stirred at 25° C. for 15 hours. LCMS showed the starting material was consumed and desired product was detected. The reaction mixture was concentrated under reduce pressure. The residue was purified by reversed phase flash (trifluoroacetic acid condition) to give compound 5 (278 mg, 1.04 mmol, 16.91% yield, 71.202% purity) as yellow solid.

LCMS: RT=0.838 min, m/z 192.1 [M+H]$^+$, purity=57.33%

$^1$H NMR (Methanol-d$_4$, 400 MHz) δ 7.58-7.55 (m, 2H), 7.26-7.23 (m, 2H), 4.82 (s, 2H), 3.74 (t, J=4.8 Hz, 2H), 3.06 (t, J=4.8 Hz, 2H).

Preparation of Compound 7

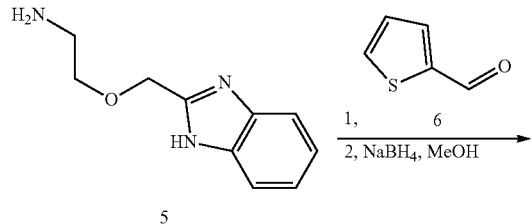

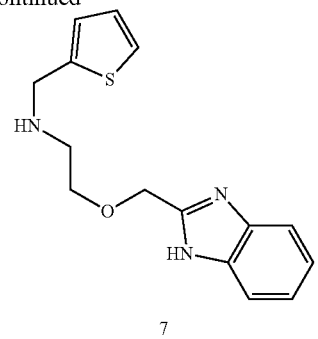
7

To a solution of compound 5 (278 mg, 1.45 mmol, 1.00 eq) in toluene (3 mL) was added compound 6 (163 mg, 1.45 mmol, 135.52 uL, 2.00 eq) and 4 A Molecular sieve (300 mg). The mixture was stirred at 100° C. for 5 hours. TLC (dichloromethane:methanol=15:1) showed the starting material was consumed. The reaction mixture was concentrated in vacuum. The residue was dissolved in methanol (3 mL), sodium borohydride (110 mg, 2.90 mmol, 2.00 eq) was added at 0° C. The reaction mixture was stirred at 0° C. for 1 hour. TLC (dichloromethane:methanol=10:1) showed the intermediate was consumed completely. The mixture was poured into 1N hydrochloric acid solution (15 mL). The mixture was stirred for 1 hour and then adjusted pH=8 with sodium bicarbonate aqueous. The mixture was extracted with ethyl acetate (40 mL*3), the combined organic layers were washed with brine (25 mL), dried over anhydrous sodium sulfate, concentrated in vacuum to give compound 7 (440 mg, 998.03 umol, 68.83% yield, 65.19% purity) as yellow oil.

LCMS: RT=1.138 min, m/z 288.1 [M+H]$^+$, purity=65.19%

$^1$H NMR (Methanol-d$_4$, 400 MHz) δ 7.54-7.52 (m, 2H), 7.27 (dd, J$_1$=4.8 Hz, J$_2$=0.8 Hz, 1H), 7.24-7.21 (m, 2H), 6.98-6.93 (m, 2H), 4.76 (s, 2H), 3.98 (s, 2H), 3.70 (t, J=4.8 Hz, 2H), 2.86 (t, J=5.2 Hz, 2H).

Preparation of Compound TDIW-167-01

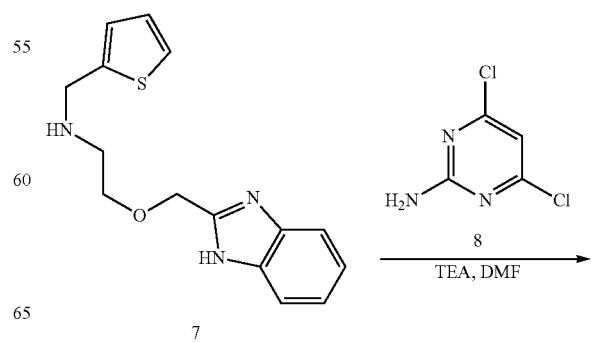

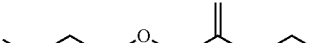

TDIW-167-01

To a solution of compound 7 (200 mg, 452.36 umol, 1.00 eq) in N, N-dimethylformamide (2 mL) was added compound 8 (111 mg, 678.54 umol, 1.50 eq) and triethylamine (137 mg, 1.36 mmol, 188.11 uL, 2.00 eq). The mixture was stirred at 120° C. for 6 hours. LCMS showed 7% of the starting material still remained and desired product was detected. The reaction mixture was quenched by water (15 mL); the solid was filtered to give a residue. The residue was purified by prep-HPLC (Column: Phenomenex Gemini 150 mm*25 mm*10 um; mobile phase: [water (0.05% ammonia hydroxide v/v)-ACN]; B %: 32%-62%, 10 min) and followed by lyophilization to give (68.10 mg, 162.93 umol, 36.02% yield, 99.27% purity) as a white solid.

LCMS: RT=2.003 min, m/z 415.0 [M+H]$^+$, purity=99.27%

$^1$H NMR (DMSO-d$_6$, 400 MHz) δ 7.54-7.52 (m, 2H), 7.37 (d, J=4.4 Hz, 1H), 7.19-7.14 (m, 2H), 7.03 (d, J=2.8 Hz, 1H), 6.93 (t, J=4.8 Hz, 1H), 6.55 (br. s, 2H), 6.06 (s, 1H), 4.88 (s, 2H), 4.70 (s, 2H), 3.67-3.52 (m, 4H).

Preparation of Compound 9

Compound 3 (4.2 g, 26.05 mmol, 4.04 mL, 1.00 eq) was added into a mixture of sodium hydride (1.67 g, 41.68 mmol, 60% purity in mineral oil, 1.60 eq) and potassium iodide (433 mg, 2.61 mmol, 0.10 eq) in tetrahydrofuran (80 mL) drop wise over a period of 20 min at 0° C. Then a solution of ethyl 2-bromoacetate (8.7 g, 52.10 mmol, 5.76 mL, 2.00 eq) in tetrahydrofuran (20 mL) was added. The mixture was stirred at 15° C. for 4 hours. TLC (petroleum ether:ethyl acetate=3:1) showed the starting material still remained and a new spot was detected. The mixture was poured into water (100 mL) and then extracted with ethyl acetate (80 mL*3), the combined organic layers were washed with brine (50 mL), dried over anhydrous sodium sulfate, concentrated in vacuum. The residue was purified by column chromatography (SiO$_2$, Petroleum ether:Ethyl acetate=30:1-10:1) to give compound 9 (3.9 g, 15.77 mmol, 60.54% yield) as light yellow liquid.

$^1$H NMR (CDCl$_3$, 400 MHz): δ 5.13 (br. s, 1H), 4.23 (q, J=7.2 Hz, 2H), 4.09 (s, 2H), 3.62 (t, J=5.2 Hz, 2H), 3.35 (t, J=5.2 Hz, 2H), 1.45 (s, 9H), 1.30 (t, J=7.2 Hz, 3H).

Preparation of Compound 10

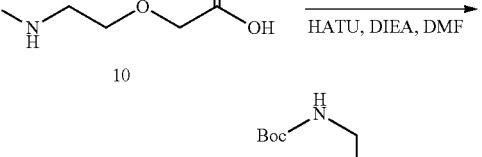

To a solution of compound 9 (3.9 g, 15.77 mmol, 1.00 eq) in tetrahydrofuran (40 mL) and water (20 mL) was added lithium hydroxide monohydrate (1.32 g, 31.54 mmol, 2.00 eq). The mixture was stirred at 15° C. for 3 hours. TLC (petroleum ether:ethyl acetate=3:1) showed the starting material was consumed completely. The mixture was acidified to pH=2 with 1 N hydrochloric acid aqueous solution, extracted with dichloromethane (70 mL*3). The combined organic layer was washed with brine (50 mL*2), dried over anhydrous sodium sulfate, concentrated in vacuum to give compound 10 (3.35 g, 15.28 mmol, 96.90% yield) as light yellow gum, which was used into the next step without further purification.

$^1$H NMR (CDCl$_3$, 400 MHz): δ 8.05 (br. s, 1H), 5.16 (br. s, 1H), 4.14 (s, 2H), 3.64 (t, J=5.2 Hz, 2H), 3.36-3.31 (m, 2H), 1.46 (s, 9H).

Preparation of Compound 11

To a solution of compound 10 (2.85 g, 13.00 mmol, 1.00 eq) and N, N-diisopropylethylamine (3.36 g, 26.00 mmol, 4.54 mL, 2.00 eq) in N, N-dimethylformamide (30 mL) was added HATU (5.93 g, 15.60 mmol, 1.20 eq) at 0° C. The mixture was stirred at 0° C. for 10 min. Aniline (1.21 g, 13.00 mmol, 1.19 mL, 1.00 eq) was added. The reaction mixture was stirred at 15° C. for 3 hours. The mixture was quenched with water (50 mL), extracted with ethyl acetate (60 mL*3). The combined organic layer was washed with 1N hydrochloric acid aqueous solution (50 mL), saturated sodium bicarbonate aqueous solution (50 mL), brine (50 mL*2) and dried over anhydrous sodium sulfate, concentrated in vacuum. The residue was purified by column chromatography (SiO$_2$, Petroleum ether:Ethyl acetate=10:1~2:1) to give compound 11 (3.15 g, 9.68 mmol, 74.43% yield, 90.42% purity) as light yellow gum.

LCMS: RT=0.852 min, m/z 317.1 [M+H]$^+$, purity=90.42%

$^1$H NMR (CDCl$_3$, 400 MHz): δ 8.45 (br. s, 1H), 7.62 (d, J=7.6 Hz, 2H), 7.36-7.32 (m, 2H), 7.13 (t, J=7.6 Hz, 1H), 4.91 (br. s, 1H), 4.09 (s, 2H), 3.66 (t, J=5.2 Hz, 2H), 3.42 (q, J=5.2 Hz, 2H), 1.45 (s, 9H).

Preparation of Compound 12

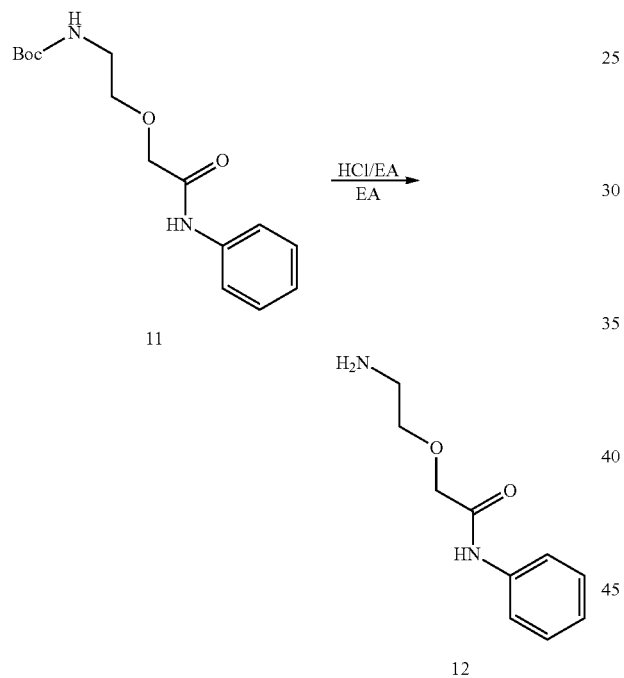

To a solution of compound 11 (1 g, 3.40 mmol, 1.00 eq) in ethyl acetate (10 mL) was added hydrochloric acid solution (4 M, 10 mL, 11.76 eq). The mixture was stirred at 15° C. for 0.5 hour, lots of solid precipitates appeared. TLC (petroleum ether:ethyl acetate=2:1) showed the starting material was consumed completely. The mixture was filtered; the solid was washed with ethyl acetate (5 mL*3), dried in vacuum to give the compound 12 (640 mg, 2.74 mmol, 80.57% yield, 98.74% purity, hydrochloride) as a white solid.

LCMS: RT=0.644 min, m/z 195.0 [M+H]$^+$, purity=98.74%

$^1$H NMR (DMSO-d$_6$, 400 MHz): δ 9.91 (s, 1H), 8.30 (br. s, 3H), 7.72 (d, J=7.6 Hz, 2H), 7.31 (t, J=7.6 Hz, 2H), 7.07 (t, J=7.6 Hz, 1H), 4.12 (s, 2H), 3.72 (t, J=5.2 Hz, 2H), 3.07-3.02 (m, 2H).

Preparation of Compound 13

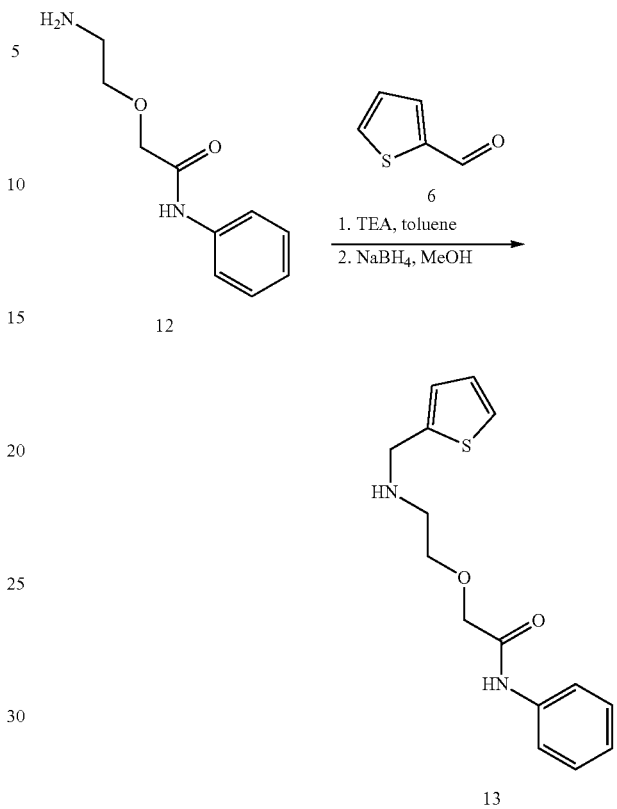

To a solution of compound 12 (200 mg, 866.96 umol, 1.00 eq, hydrochloride) and triethylamine (105 mg, 1.04 mmol, 144.21 uL, 1.20 eq) in toluene (3 mL) was added compound 6 (97 mg, 866.96 umol, 81.03 uL, 1.00 eq) and 4 A Molecular sieve (100 mg). The mixture was stirred at 100° C. for 5 hours under nitrogen atmosphere. TLC (dichloromethane:methanol=10:1) showed most of the starting material was consumed. The mixture was concentrated in vacuum, the residue was dissolved in methanol (3 mL), sodium borohydride (66 mg, 1.73 mmol, 2.00 eq) was added at 0° C. The reaction mixture was stirred at 0° C. for 1 hour. TLC (petroleum ether:ethyl acetate=1:1) showed the intermediate was consumed completely. The mixture was poured into 1 N hydrochloric acid aqueous solution (20 mL). The mixture was stirred at 15° C. for 1 hour and then adjusted to pH=8 with sodium bicarbonate aqueous. The mixture was extracted with dichloromethane (30 mL*3). The combined organic layer was washed with brine (20 mL), dried over anhydrous sodium sulfate, concentrated in vacuum. The residue was purified by column chromatography (SiO$_2$, Petroleum ether:Ethyl acetate=10:1-1:1) to give compound 13 (113 mg, 389.15 umol, 44.89% yield, 100.00% purity) as light yellow gum.

LCMS: RT=0.878 min, m/z 291.0 [M+H]$^+$, purity=100.00%

$^1$H NMR (CDCl$_3$, 400 MHz): δ 9.05 (br. s, 1H), 7.59 (d, J=7.6 Hz, 2H), 7.34-7.30 (m, 2H), 7.24 (dd, J$_1$=4.8 Hz, J$_2$=1.2 Hz, 1H), 7.12 (d, J=7.6 Hz, 1H), 6.98-6.95 (m, 2H), 4.10 (s, 2H), 4.09 (s, 2H), 3.71 (t, J=5.2 Hz, 2H), 2.93 (t, J=5.2 Hz, 2H).

Preparation of TDIW-167-02

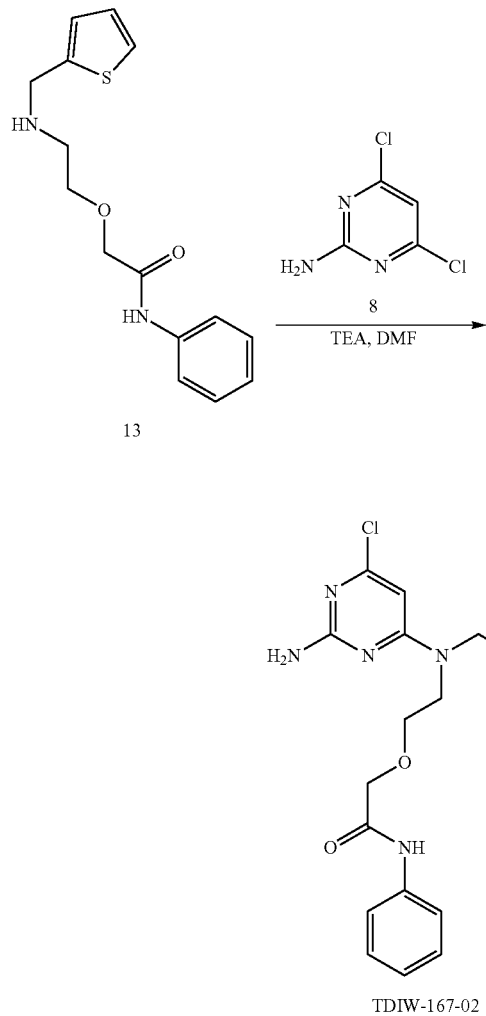

TDIW-167-02

To a solution of compound 13 (60 mg, 206.63 umol, 1.00 eq) and compound 8 (51 mg, 309.95 umol, 1.50 eq) in N, N-dimethylformamide (2 mL) was added triethylamine (63 mg, 619.89 umol, 85.93 uL, 3.00 eq). The mixture was stirred at 120° C. for 6 hours. TLC (petroleum ether:ethyl acetate=1:1) showed most of the starting material was consumed. The mixture was poured into water (20 mL), extracted with ethyl acetate (20 mL*3). The combined organic layer was washed with brine (20 mL*3), dried over anhydrous sodium sulfate, concentrated in vacuum. The residue was purified by prep-HPLC (column: Phenomenex Gemini C18 250 mm*50 mm*10 um; mobile phase: [water (0.05% ammonia hydroxide v/v)-ACN]; B %: 35%-65%, 12 min) and followed by lyophilization to give TDIW-167-02 (30.20 mg, 71.95 umol, 34.82% yield, 99.56% purity) as a grey solid.

LCMS: RT=2.761 min, m/z 418.4 [M+H]$^+$, purity=99.56%

$^1$H NMR (CDCl$_3$, 400 MHz): δ 8.05 (br. s, 1H), 7.46 (d, J=8.0 Hz, 2H), 7.34 (t, J=8.0 Hz, 2H), 7.23 (dd, J$_1$=5.2 Hz, J$_2$=1.2 Hz, 1H), 7.13 (d, J=7.6 Hz, 1H), 6.97-6.95 (m, 2H), 6.09 (s, 1H), 4.90-4.89 (m, 4H), 4.05 (s, 2H), 3.76 (s, 4H).

Preparation of Compound 15

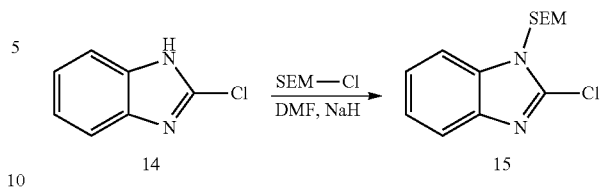

To a solution of compound 14 (2 g, 13.11 mmol, 1.00 eq) in N, N-dimethylformamide (15 mL) was added sodium hydride (629 mg, 15.73 mmol, 60% purity, 1.20 eq) at 0° C. The mixture was stirred at 0° C. for 10 min, a solution of 2-(trimethylsilyl)ethoxymethyl chloride (2.62 g, 15.73 mmol, 2.79 mL, 1.20 eq) in N, N-dimethylformamide (5 mL) was added drop wise at 0° C. The reaction mixture was stirred at 0° C. for 0.5 hour. TLC (petroleum ether:ethyl acetate=1:1) and LCMS showed the starting material was consumed completely. The mixture was poured into s saturated ammonium chloride solution (150 mL), extracted with ethyl acetate (80 mL*3). The combined organic layer was washed with brine (50 mL*3), dried over anhydrous sodium sulfate, concentrated in vacuum. The residue was purified by column chromatography (SiO$_2$, Petroleum ether:ethyl acetate=35:1~20:1) to give compound 15 (2.47 g, 6.65 mmol, 50.71% yield, 76.13% purity) as a white solid.

LCMS: RT=0.923 min, m/z 283.0, 285.0 [M+H]$^+$, purity=76.13%

$^1$H NMR (CDCl$_3$, 400 MHz): δ 7.71-7.70 (m, 1H), 7.49-7.46 (m, 1H), 7.34-7.30 (m, 2H), 5.58 (s, 2H), 3.59 (d, J=8.0 Hz, 2H), 0.92 (d, J=8.0 Hz, 2H), -0.04 (s, 9H).

Preparation of Compound 17

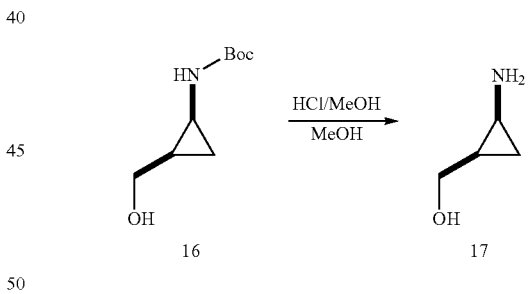

To a solution of compound 16 (100 mg, 534.07 umol, 1.00 eq) in methanol (1 mL) was added the solution of hydrochloric acid in methanol (4 M, 1.00 mL, 7.49 eq). The mixture was stirred at 15° C. for 0.5 hour. TLC (petroleum ether:ethyl acetate=1:1) showed the starting material was consumed. The mixture was concentrated in vacuum to give compound 17 (70 mg, crude, hydrochloride) as a brown solid, which was used into the next step without further purification.

Note: A relatively configuration of the material 16 was used as starting material.

$^1$H NMR (methanol-d$_4$, 400 MHz): δ 4.02 (dd, J$_1$=11.6 Hz, J$_2$=4.0 Hz, 1H), 3.78 (dd, J$_1$=11.6 Hz, J$_2$=6.0 Hz, 1H), 2.73-2.69 (m, 1H), 1.39-1.31 (m, 1H), 1.06-1.02 (m, 1H), 0.90-0.80 (m, 1H).

Preparation of Compound 18

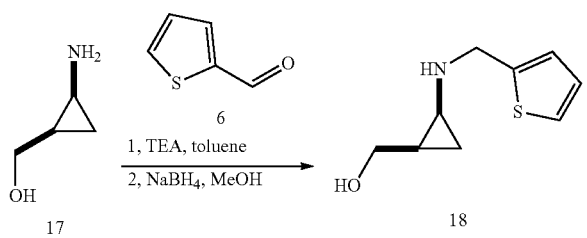

To a solution of compound 17 (45 mg, 364.14 umol, 1.00 eq, hydrochloride) and triethylamine (74 mg, 728.27 umol, 100.95 uL, 2.00 eq) in toluene (0.2 mL) was added compound 6 (41 mg, 364.14 umol, 34.03 uL, 1.00 eq). The mixture was stirred at 100° C. for 5 hours. The reaction mixture was concentrated in vacuum. The residue was dissolved in methanol (0.2 mL); sodium borohydride (28 mg, 728.27 umol, 2.00 eq) was added at 0° C. The reaction mixture was stirred at 15° C. for 0.5 hour. LCMS showed desired product was detected. The mixture was quenched with 1N hydrochloric acid aqueous solution (5 mL). The mixture was stirred at 15 min and then neutralized with saturated sodium bicarbonate solution to pH=7-8. The mixture was extracted with dichloromethane (30 mL*5); the combined organic layer was dried over anhydrous sodium sulfate, concentrated in vacuum. The residue was purified by prep-TLC (SiO$_2$, petroleum ether:ethyl acetate=0:1) to give compound 18 (50 mg, 272.82 umol, 74.92% yield, 100% purity) as light yellow oil.

Note: SFC shown enantiomers were detected.

LCMS: RT=0.754 min, m/z 184.0 [M+H]$^+$, purity=100.00%

$^1$H NMR (CDCl$_3$, 400 MHz): δ 7.22 (dd, J$_1$=4.8 Hz, J$_2$=1.6 Hz, 1H), 6.97-6.94 (m, 2H), 4.06-4.03 (m, 3H), 3.89 (dd, J$_1$=11.6 Hz, J$_2$=4.8 Hz, 1H), 2.54 (br. s, 2H), 2.44-2.39 (m, 1H), 1.00-0.99 (m, 1H), 0.76-0.68 (m, 2H).

Preparation of Compound 19

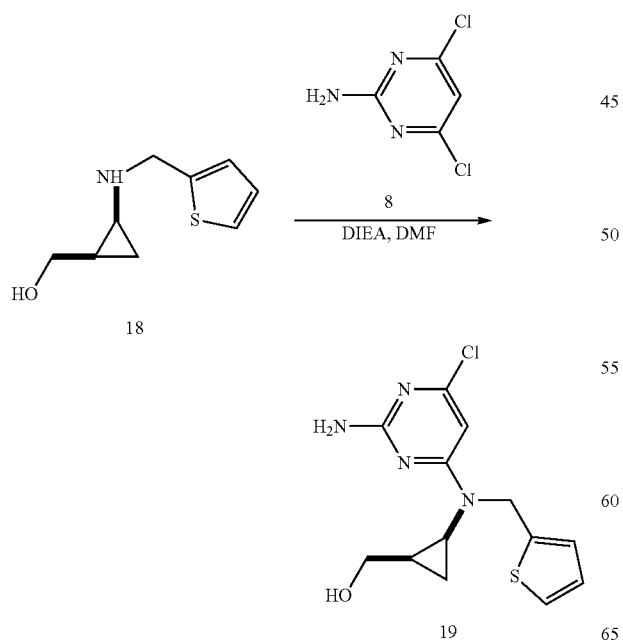

To a solution of compound 18 (400 mg, 2.18 mmol, 1.00 eq) and compound 8 (429 mg, 2.62 mmol, 1.20 eq) in dimethyl formamide (5 mL) was added N, N-diisopropylethylamine (563 mg, 4.36 mmol, 761.47 uL, 2.00 eq). The mixture was stirred at 100° C. for 42 hours. LCMS showed compound 18 still remained. Another 43 mg of compound 8 was added and the reaction mixture was stirred at 100° C. for 24 hours. The mixture was concentrated in vacuum; the residue was diluted with dichloromethane (60 mL) and then washed with brine (20 mL). The organic layer was dried over anhydrous sodium sulfate, concentrated in vacuum, the residue was purified by prep-TLC (SiO$_2$, petroleum ether:ethyl acetate=1:1) to give compound 19 (230 mg, 638.12 umol, 29.27% yield, 86.22% purity) as a yellow solid.

LCMS: RT=0.820 min, m/z 311.0, 313.0 [M+H]$^+$, purity=86.22%

$^1$H NMR (CDCl$_3$, 400 MHz): δ 7.19 (dd, J$_1$=4.8 Hz, J$_2$=1.6 Hz, 1H), 7.00-6.94 (m, 3H), 6.26 (s, 1H), 5.08 (d, J=16.0 Hz, 1H), 5.00 (s, 2H), 4.72 (d, J=16.0 Hz, 1H), 3.70-3.66 (m, 1H), 3.44-3.40 (m, 1H), 2.73-2.68 (m, 1H), 1.56-1.55 (m, 1H), 1.14-1.10 (m, 1H), 0.73-0.72 (m, 1H).

Preparation of Compound 20

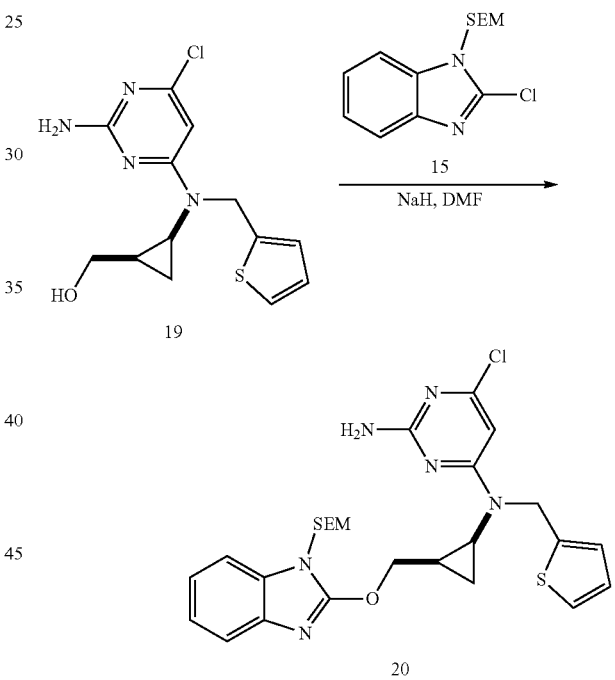

To a solution of compound 19 (50 mg, 160.87 umol, 1.00 eq) in N, N-dimethylformamide (0.2 mL) was added sodium hydride (8 mg, 209.14 umol, 60% purity, 1.30 eq). The mixture was stirred at 15° C. for 10 min. Compound 15 (55 mg, 193.05 umol, 1.20 eq) was added. The reaction mixture was stirred at 15° C. for 6 hours. LCMS and TLC (petroleum ether:ethyl acetate=2:1) showed the starting material was consumed. The mixture was poured into water (10 mL) and then extracted with ethyl acetate (30 mL*3). The combined organic layer was washed with brine (20 mL*3), dried over anhydrous sodium sulfate, concentrated in vacuum. The residue was purified by prep-HPLC (column: Phenomenex Gemini 150 mm*25 mm*10 um; mobile phase: [water (0.05% ammonia hydroxide v/v)—ACN]; B %: 65%-95%, 10 mins) to give compound 20 (30 mg, 53.84 umol, 33.47% yield, 100% purity) as a white solid.

LCMS: RT=1.150 min, m/z 579.2, 581.2 [M+Na]+, purity=100.00%

¹H NMR (DMSO-d₆, 400 MHz): δ 7.41-7.34 (m, 3H), 7.11-7.09 (m, 2H), 7.06 (d, J=2.8 Hz, 1H), 6.96-6.94 (m, 1H), 6.67 (br. s, 2H), 6.23 (s, 1H), 5.36-5.34 (m, 3H), 4.66 (d, J=15.2 Hz, 1H), 4.42-4.29 (m, 2H), 3.50 (t, J=8.0 Hz, 2H), 2.71-2.67 (m, 1H), 1.87-1.78 (m, 1H), 1.23-1.17 (m, 1H), 1.11-1.08 (m, 1H), 0.80 (t, J=8.0 Hz, 2H), −0.10 (s, 9H).

Preparation of Compound TDIW-167-03

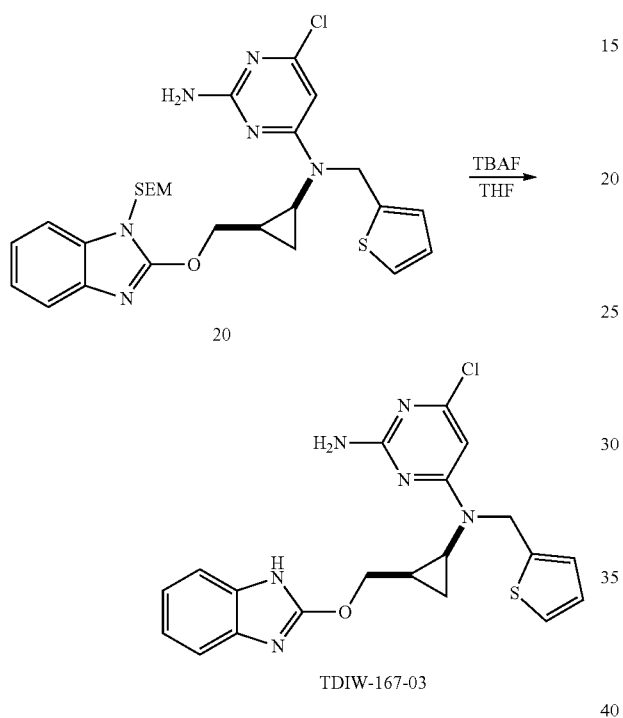

To a solution of compound 20 (30 mg, 53.84 umol, 1 eq) in tetrahydrofuran (0.5 mL) was added tetrabutylammonium fluoride trihydrate (153 mg, 484.58 umol, 9 eq). The mixture was stirred at 80° C. for 18 hours. TLC (petroleum ether: ethyl acetate=1:1) and LCMS showed the starting material was consumed. The mixture was diluted with ethyl acetate (60 mL) and then washed with brine (20 mL*3). The organic layer was dried over anhydrous sodium sulfate, concentrated in vacuum. The residue was purified by prep-TLC (SiO₂, petroleum ether:ethyl acetate=1:1) to give compound TDIW-167-03 (9.2 mg, 21.55 umol, 40.02% yield, 100% purity) as a white solid.

LCMS: RT=0.946 min, m/z 449.3 [M+Na]⁺, purity=100.00%

¹H NMR (Methanol-d₄, 400 MHz): δ 7.34-7.21 (m, 3H), 7.08-7.05 (m, 3H), 6.91-6.89 (m, 1H), 6.34 (s, 1H), 5.33 (d, J=15.6 Hz, 1H), 4.79 (d, J=15.2 Hz, 1H), 4.48-4.43 (m, 1H), 4.27-4.25 (m, 1H), 2.76-2.72 (m, 1H), 1.88-1.83 (m, 1H), 1.30-1.25 (m, 1H), 1.07-1.04 (m, 1H).

While the disclosure has been particularly shown and described with reference to specific embodiments, it should be understood by those having skill in the art that various changes in form and detail may be made therein without departing from the spirit and scope of the disclosure.

What is claimed is:

1. A compound having the following structure:

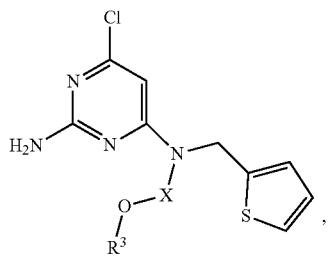

wherein

X is a substituted or unsubstituted $C_1$ to $C_3$ aliphatic group and $R^3$ is selected from the group consisting of:

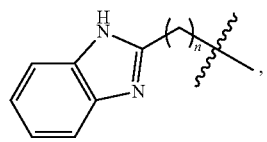

wherein n is 0 or 1, and

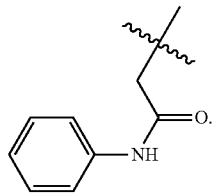 [SMILES: *CC(=O)Nc1ccccc1]

2. The compound of claim 1, wherein X is an unsubstituted $C_1$ to $C_3$ alkanediyl group having the following structure:

and m is 2 or 3.

3. The compound of claim 1, wherein X is an unsubstituted $C_1$ to $C_3$ aliphatic group having the following structure:

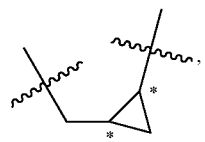 [SMILES: *CC1CC1*]

wherein *, individually at each occurrence, indicate R or S stereochemistry.

4. The compound of claim 1, wherein the compound has one of the following structures:

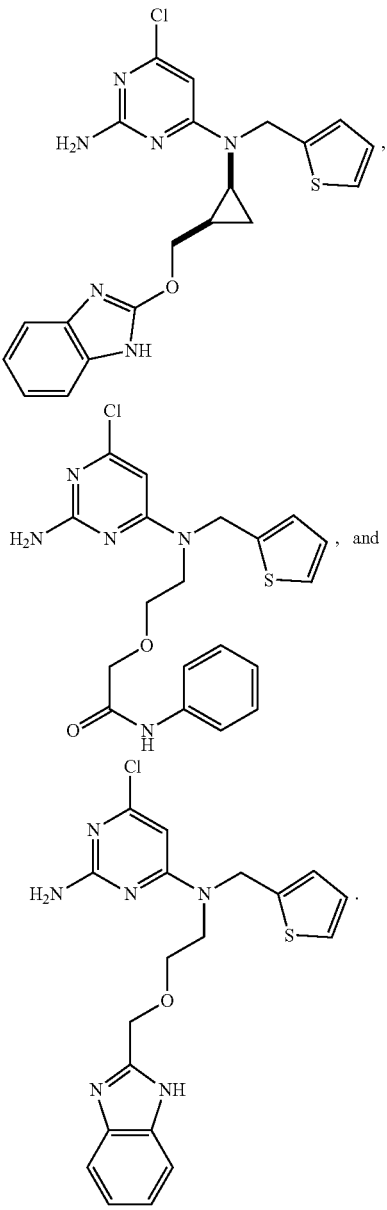

5. A composition comprising a pharmaceutically acceptable carrier and one or more compounds having the following structure:

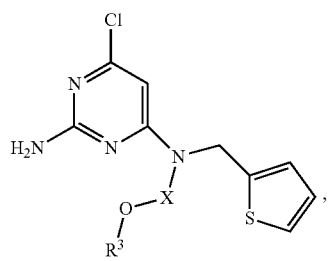

wherein
X is a substituted or unsubstituted $C_1$ to $C_3$ aliphatic group and $R^3$ is selected from the group consisting of:

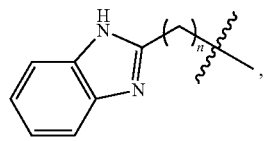

wherein n is 0 or 1, and

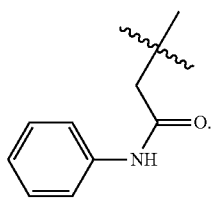 [SMILES: *CC(=O)Nc1ccccc1]

or

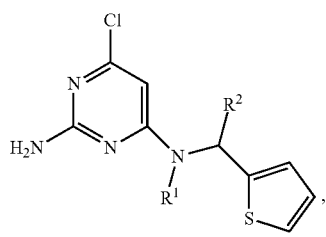

wherein
$R^1$ is:

wherein r is 1, 2, 3, 4, or 5;

wherein s is 1, 2, 3, 4, or 5; or

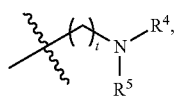

wherein t is 1, 2, 3, 4, or 5, and
$R^4$ and $R^5$ are each independently a substituted or unsubstituted $C_1$-$C_5$ alkyl group, and
$R^2$ is H or a substituted or unsubstituted phenyl group, with the proviso the compound does not have the following structure:

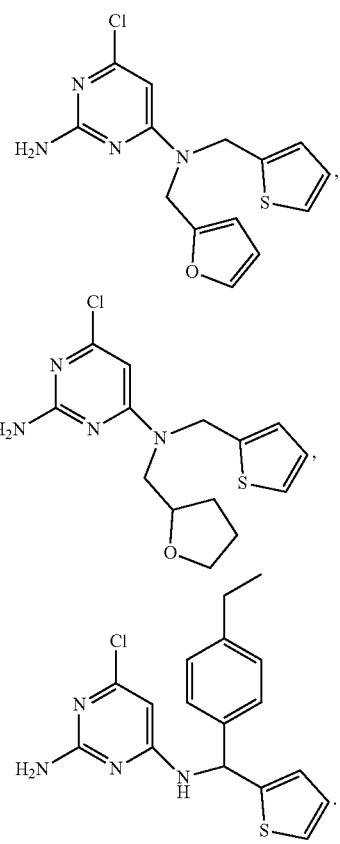

6. The composition of claim 5, wherein $R^2$ is a substituted phenyl group having the following structure:

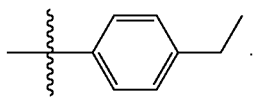

7. The composition of claim 5, wherein X is an unsubstituted $C_1$ to $C_3$ alkanediyl group having the following structure:

and m is 2 or 3.

8. The composition of claim 5, wherein X is a $C_1$ to $C_3$ aliphatic group having the following structure:

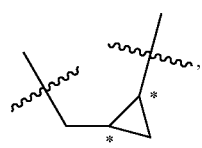

wherein *, individually at each occurrence, indicate R or S stereochemistry.

9. The composition of claim 5, wherein the one or more compounds is selected from the group consisting of:

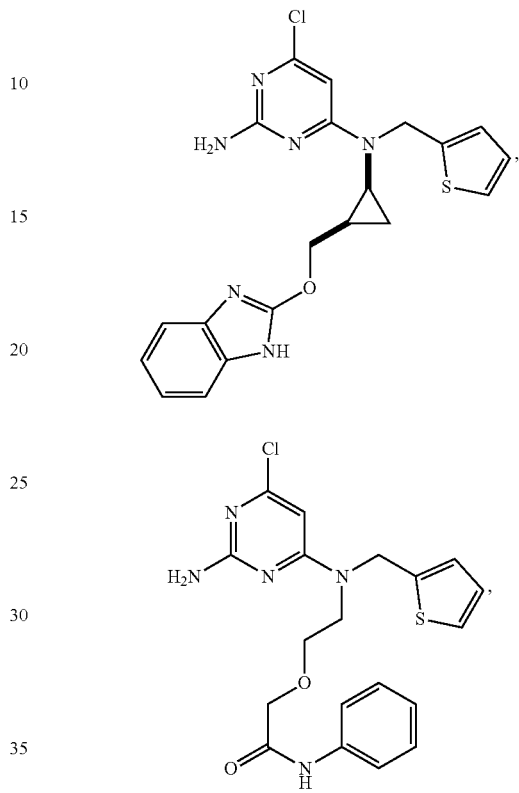

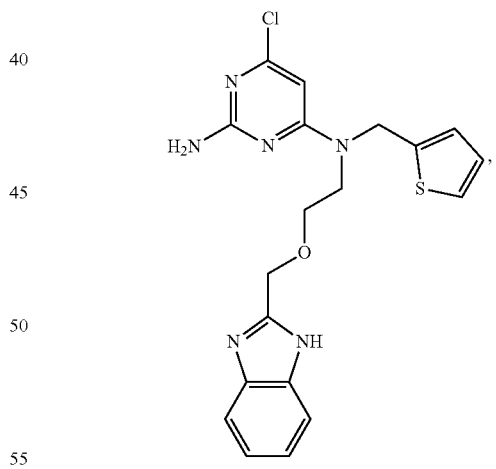

and combinations thereof.

10. A method of treatment of ocular hypotony comprising administering to an individual in need of treatment a composition of claim 5.

11. The method of claim 10, wherein the individual has been surgically treated for glaucoma.

* * * * *

UNITED STATES PATENT AND TRADEMARK OFFICE
CERTIFICATE OF CORRECTION

PATENT NO. : 10,981,899 B2  
APPLICATION NO. : 16/097087  
DATED : April 20, 2021  
INVENTOR(S) : Buck et al.

Page 1 of 1

It is certified that error appears in the above-identified patent and that said Letters Patent is hereby corrected as shown below:

In the Claims

Column 45, Lines 25-34, in Claim 5, the structure should read:

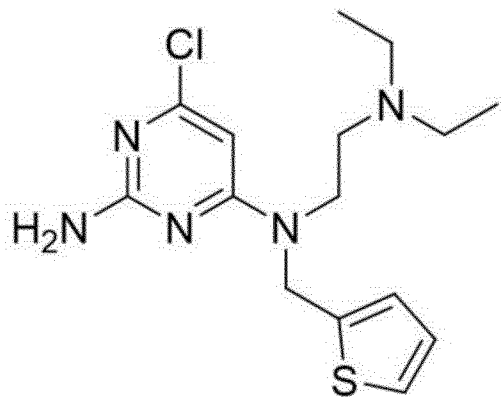

-- --

Signed and Sealed this  
Sixteenth Day of November, 2021

Drew Hirshfeld  
*Performing the Functions and Duties of the*  
*Under Secretary of Commerce for Intellectual Property and*  
*Director of the United States Patent and Trademark Office*